United States Patent
Green et al.

(10) Patent No.: US 7,271,181 B2
(45) Date of Patent: Sep. 18, 2007

(54) INHIBITORS OF P38

(75) Inventors: Jeremy Green, Burlington, MA (US); Scott L Harbeson, Cambridge, MA (US); John E Cochran, North Andover, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/144,153

(22) Filed: May 10, 2002

(65) Prior Publication Data

US 2003/0096817 A1    May 22, 2003

Related U.S. Application Data

(60) Provisional application No. 60/290,504, filed on May 11, 2001.

(51) Int. Cl.
    C07D 401/12    (2006.01)
    C07D 401/14    (2006.01)
    C07D 403/12    (2006.01)
    C07D 403/14    (2006.01)
    A61K 31/44     (2006.01)
    A61P 9/10      (2006.01)
    A61P 19/02     (2006.01)

(52) U.S. Cl. ............ 514/336; 514/345; 514/349; 514/350; 514/231.5; 514/252.1; 546/268.1; 546/290; 546/297; 544/111; 544/359

(58) Field of Classification Search ............ 546/268.1, 546/290, 297; 514/336, 345, 349, 300, 350, 514/250
See application file for complete search history.

(56) References Cited

U.S. PATENT DOCUMENTS

| | | | | |
|---|---|---|---|---|
| 3,499,898 A | * | 3/1970 | Thiele et al. | 544/332 |
| 3,506,668 A | * | 4/1970 | Lesher | 546/153 |
| 3,819,639 A | | 6/1974 | Delarge et al. | 260/294.8 |
| 4,973,690 A | | 11/1990 | Rempfler et al. | 544/279 |
| 5,498,609 A | * | 3/1996 | Ogawa et al. | 540/293 |
| 5,677,299 A | * | 10/1997 | Ogawa et al. | 514/221 |
| 5,753,648 A | | 5/1998 | Albright et al. | 514/220 |
| 6,316,474 B1 | | 11/2001 | McCauley et al. | |
| 6,586,423 B2 | | 7/2003 | Bilodeau et al. | |
| 6,586,424 B2 | | 7/2003 | Bilodeau et al. | |
| 6,919,336 B2 | | 7/2005 | Révész | |

FOREIGN PATENT DOCUMENTS

| | | |
|---|---|---|
| WO | WO97/09325 | 3/1997 |
| WO | WO99/58502 | 11/1999 |
| WO | WO01/17995 A1 | 3/2001 |
| WO | WO01/32174 A1 | 5/2001 |
| WO | WO02/076447 A1 | 10/2002 |

OTHER PUBLICATIONS

Graninger et al. Curr. Opin. Rheumatol. 13(3): 209-213, 2001.*
Brunet et al., Esaays Biochem. 32 : 1-16, 1997.*
Nagarkatti et al. J. Mol. Cell Cardiol. 30(8): 1651-1664, 1998.*
Herlaar et al. Mol. Med. Today 5(10) 439-447,1999.*
Jefferson, W. Tilley et al., "A Palladium-Catalyzed Carbonyl Insertion Route to Pyrido[2,1-b]quinazoline Derivatives," J. Org. Chem., 52, 2469-2474 (1987).
V. P. Arya et al., Ind. J. Chem. Sect. B, 15, 1129-1132 (1977), Beilstein Registry No. 819099, 824847.
W. H. Nyberg et al., J. Het. Chem., 1, 1-5 (1964), Beilstein Registry No. 531011, 532897.
Korytnyk et al., "Guanylhydrazones with Potential Antileukemic Activity. 1. Aza Analogs of 4,4'-Diacetyldiphenylurea Bis (guanylhydrazone)", Journal of Medicinal Chemistry, 1973, vol. 16, No. 8, pp. 959-961.
Nyberg et al., Beilstein Registry No. 521505.
Wright et al., Beilstein Registry Nos. 7989593, 7990821, 8000138.
Gueremy et al., "2-Amino-6-chloro-4-(N-methylpiperazino) pyrimidines, Inhibitors of Spiroperidol Binding", Journal of Medicinal Chemistry, 1982, vol. 25, pp. 1459-1465.
Revesz et al., "SAR of benzoylpyridines and penzophenones as p38α MAP kinase inhibitors with oral activity", Bioorganic & Medicinal Chemistry Letters, 2004, vol. 14, pp. 3601-3605.

* cited by examiner

*Primary Examiner*—Venkataraman Balasubramanian
(74) *Attorney, Agent, or Firm*—Ropes & Gray LLP; James F. Haley, Jr.; David A. Roise

(57) ABSTRACT

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

15 Claims, No Drawings

INHIBITORS OF P38

This application claims the benefit of U.S. Provisional Application No. 60/290,504, filed May 11, 2001, which is herein incorporated by reference.

TECHNICAL FIELD OF INVENTION

The present invention relates to inhibitors of p38, a mammalian protein kinase involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., Ann. Rep. Med. Chem., 31, pp. 289-98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor, CD14, and induced with LPS. p38 has since been isolated and sequenced, as has the cDNA encoding it in humans and mouse. Activation of p38 has been observed in cells stimulated by stress, such as treatment of lipopolysaccharides (LPS), UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., Endocrinol., 136, pp. 3054-61 (1995)].

Based upon this finding, it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have also been implicated in the area of pain management through inhibition of prostaglandin endoperoxide synthase-2 induction. Other diseases associated with Il-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and, in particular, p38. However, the efficacy of these inhibitors in vivo is still being investigated.

Other p38 inhibitors have been produced, including those described in WO 98/27098, WO 99/00357, WO 99/10291, WO 99/58502, WO 99/64400, WO 00/17175 and WO 00/17204. In addition, WO 97/24328, WO 98/34920, WO 98/35958 and U.S. Pat. No. 5,145,857 disclose amino-substituted heterocycles having therapeutic uses. However, none of the disclosed therapeutic uses include inhibition of p38 or other serine/threonine protein kinases.

Accordingly, there is still a great need to develop other potent inhibitors of p38, including p38-specific inhibitors, that are useful in treating various conditions associated with p38 activation.

SUMMARY OF THE INVENTION

The present invention addresses this problem by providing compounds that demonstrate inhibition of p38.

These compounds have the general formulae:

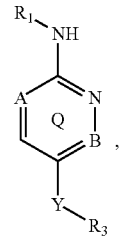
(I)

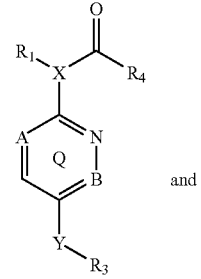
(II)
and

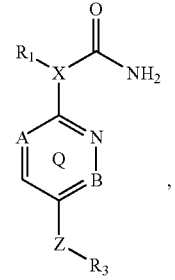
(III)

or a pharmaceutically acceptable derivative thereof, wherein:

A is N or CR.

B is N or CR.

X is N or CH.

Y is C(O), CHOH, $CH_2$, S, S(O), $S(O)_2$, NH, NR, O or Z.

Z is CHOH, —[($C_2$-$C_3$)-alkyl]-, —S—[($C_1$-$C_3$)-alkyl]-, —O—[($C_1$-$C_3$)-alkyl]-, —NH—[($C_1$-$C_3$)-alkyl]-, —[($C_2$-$C_3$)-alkenyl]-, —[($C_2$-$C_3$)-alkynyl]-, —O—[($C_2$-$C_3$)-alkenyl]-, —O—[($C_2$-$C_3$)-alkynyl]-, —S—[($C_2$-$C_3$)-alkenyl]-, —S—[($C_2$-$C_3$)-alkynyl]-, —NH—[($C_2$-$C_3$)-alkenyl]-, —NH—[($C_2$-$C_3$)-alkynyl]-, —[($C_1$-$C_3$)-alkyl]-S—, —[($C_1$-$C_3$)-alkyl]-O—, —[($C_1$-$C_3$)-alkyl]-NH—, —[($C_2$-$C_3$)-alkenyl]-O—, —[($C_2$-$C_3$)-alkynyl]-O—, —[($C_2$-$C_3$)-alkenyl]-S—, —[($C_2$-$C_3$)-alkynyl]-S—, —[($C_2$-$C_3$)-alkenyl]-NH— or —[($C_2$-$C_3$)-alkynyl]-NH—.

The carbon atoms of Q may be optionally substituted with R.

$R_1$ is selected from aryl, heteroaryl, carbocyclyl, heterocyclyl or $C_{1-10}$ aliphatic, any of which may be optionally substituted.

$R_3$ is selected from aryl, heteroaryl, carbocyclyl, heterocyclyl, or $C_{1-10}$ aliphatic, any of which may be optionally substituted.

$R_4$ is selected from $NHR_5$, $N(R_5)_2$, $OR_5$, $C(O)OR_5$, —$C(O)R_5$ or $R_6$.

Each $R_5$ is independently selected from aryl, heteroaryl, carbocyclyl, heterocyclyl or $C_{1-5}$ aliphatic;

$R_3$ is selected from aryl, heteroaryl, carbocyclyl, heterocyclyl or $C_{1-5}$ aliphatic, any of which may be optionally substituted.

Each R is independently selected from H, halo or a straight or branched chain $C_1$-$C_4$ alkyl.

Each of $R_1$, $R_5$ and $R_6$ are independently and optionally substituted with up to 4 substituents, each of which is independently selected from halo; $C_1$-$C_3$ alkyl optionally substituted with $NR'_2$, $OR'$, $CO_2R'$ or $CONR'_2$; O—($C_1$-$C_3$)-alkyl optionally substituted with $NR'_2$, $OR'$, $CO_2R'$ or $CONR'_2$; $NR'_2$; $OCF_3$; $CF_3$; $NO_2$; $CO_2R'$; $CONR'$; $SR'$; $COR'$; $S(O_2)N(R')_2$; $SCF_3$; CN; $N(R')C(O)R'$; $N(R')C(O)OR'$; $N(R')C(O)C(O)R'$; $N(R')S(O_2)R'$; $OR'$; $OC(O)R'$; $OP(O)_3H_2$; or N=C—$N(R')_2$.

$R_3$ is optionally substituted with up to 4 substituents, each of which is independently selected from halo; $C_1$-$C_3$ straight or branched alkyl optionally substituted with $N(R')_2$, $OR'$, $CO_2R'$, $S(O_2)N(R')_2$, N=C—$N(R')_2$, R', or $CON(R')_2$; O—($C_1$-$C_3$)-alkyl optionally substituted with $N(R')_2$, $OR'$, $CO_2R'$, $S(O_2)N(R')_2$, N=C—$N(R')_2$, R', or $CON(R')_2$; $N(R')_2$; $OCF_3$; $CF_3$; $NO_2$; $CON(R')_2$; R'; $OR'$; $SR'$; $COR'$; $C(O)OR'$; $S(O_2)N(R')_2$; $SCF_3$; N=C—$N(R')_2$; or CN.

R' is selected from hydrogen; ($C_1$-$C_3$)-alkyl; ($C_2$-$C_3$)-alkenyl or alkynyl; a 5-8 membered aryl ring system, a 5-8 membered heteroaryl ring system or a 5-6 membered heterocyclic ring system, any of which may be independently and optionally substituted with 1 to 3 substituents independently selected from halo, methoxy, cyano, nitro, amino, hydroxy, methyl or ethyl.

Provided that in compounds of Formula I, when A is C, B is N, Y is CHOH, O, S, $CH_2$ or NH, and $R_3$ is an N-containing heteroaryl, then $R_1$ is not aryl, carbocyclyl or pyridyl;

when A is N, B is C, Y is C=O and $R_3$ is a $C_1$-$C_8$ alkyl, $C_6$-$C_{12}$ aryl or $C_7$-$C_{12}$ aralkyl, then $R_1$ is not 1-pyrroline or 1-indole; or when A and B are both C, Y is CHOH or $CH_2$, and $R_3$ is a substituted phenyl, then $R_1$ is not cyclopropyl or benzyl.

Further provided that in compounds of Formula II, when X is N, A and B are both C, Y is $CH_2$ or O, $R_3$ is a $C_{1-5}$ aliphatic, $R_4$ is $NHR_5$, $N(R_5)_2$, or a $C_{1-4}$ aliphatic substituted with a substituted or unsubstituted piperadine or piperazine; then $R_1$ is not $CH_3$ or a ring system comprising a six-membered heteroaryl; or in compounds of Formulae I and II, when X, if present, is N, A and B are both C, Y is $CH_2$, $R_1$ is a $C_{1-8}$ aliphatic or is phenyl, $R_4$, if present, is a $C_{1-6}$ aliphatic or is phenyl, and $R_3$ is a substituted $C_5$ alkyl or is methylene substituted with 4-hydroxy-tetrahydro-pyran-2-one, then Q is not simultaneously substituted with (a) a $C_{6-10}$ optionally substituted aryl, (b) $C_{1-10}$ aliphatic or carbocyclyl, and (c) a substituted $C_6$ alkyl or alkene, ethyl or ethylene substituted with 4-hydroxy-tetrahydro-pyran-2-one, $CH_2O$ subsited with H, $C_{1-10}$ aliphatic, halo, phenyl, $C_{6-10}$ aryl or a carbonyl substituted with $C_{1-8}$ aliphatic or phenyl.

In another embodiment, the invention provides pharmaceutical compositions comprising a p38 inhibitor of this invention. These compositions may be utilized in methods for treating or preventing a variety of p38-mediated disorders, such as cancer, inflammatory diseases, autoimmune diseases, destructive bone disorders, proliferative disorders, infectious diseases, viral diseases and neurodegenerative diseases. These compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. Each of these above-described methods is also part of the present invention.

In another embodiment, the invention provides methods of synthesizing compounds of formula I and pharmaceutical compositions comprising these compounds.

DETAILED DESCRIPTION OF THE INVENTION

As used herein, the following definitions shall apply unless otherwise indicated. Also, combinations of substituents or variables are permissible only if such combinations result in stable compounds.

The term "aliphatic" as used herein refers to a straight chained or branched hydrocarbon that is completely saturated or that contains one or more units of unsaturation. For example, aliphatic groups include substituted or unsubstituted linear or branched alkyl, alkenyl and alkynyl groups. Unless indicated otherwise, the term "aliphatic" encompasses both substituted and unsubstituted hydrocarbons. The term "alkyl" refers to both straight and branched saturated chains containing one to twelve carbon atoms. The terms "alkenyl" and "alkynyl" encompasses both straight and branched chains containing two to twelve carbon atoms and at least one unit of unsaturation.

The term "halogen" or "halo" means F, Cl, Br, or I.

The term "heteroatom" means N, O, or S and shall include any oxidized form of nitrogen and sulfur, such as N(O), S(O), $S(O)_2$ and the quaternized form of any basic nitrogen.

The term "carbocyclic" or "carbocyclyl" refers to a non-aromatic carbocyclic ring. A carbocyclic ring can be three to eight-membered. Further, a carbocyclic ring may be fused to another ring, such as a heterocyclic, aryl or heteroaryl ring, or another carbocyclic ring. A carbocyclic ring system may be monocyclic, bicyclic or tricyclic. The term "carbocyclic ring", whether saturated or unsaturated, also refers to rings that are optionally substituted unless indicated.

The term "heterocyclic" or "heterocyclyl" refers to a non-aromatic heterocyclic ring in which one or more ring carbons in a non-aromatic carbocyclic ring is replaced by a heteroatom such as nitrogen, oxygen or sulfur in the ring. One having ordinary skill in the art will recognize that the maximum number of heteroatoms in a stable, chemically feasible heterocyclic ring is determined by the size of the ring, degree of unsaturation, and valence.

In general, a heterocyclic ring may have one to four heteroatoms so long as the heterocyclic ring is chemically feasible and stable. The ring can be five, six, seven or eight-membered and/or fused to another ring, such as a carbocyclic, aryl or heteroaryl ring or to another heterocyclic ring. A heterocyclic ring system may be monocyclic, bicyclic or tricyclic. The term "heterocyclic ring", whether saturated or unsaturated, also refers to rings that are optionally substituted, unless otherwise indicated.

Examples of heterocyclic rings include, without limitation, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane.

The term "aryl" refers to monocyclic, bicyclic or tricyclic carbocyclic aromatic ring systems having five to fourteen members. The term "aralkyl" refers to a aryl group comprising a ($C_1$-$C_3$) alkyl group, wherein the alkyl group links the aralkyl group to the remainder of the molecule. Examples of aralkyl groups include benzyl and phenethyl. The term "aryl" includes aralkyl ring systems unless otherwise indicated. Aryl groups include, without limitation, phenyl, 1-naphthyl, 2-naphthyl, 1-anthracyl and 2-anthracyl. The term "aryl", "aryl group" or "aryl ring" also refers to rings that are optionally substituted, unless otherwise indicated.

The term "heteroaryl" refers to monocyclic, bicyclic or tricyclic heterocyclic aromatic ring systems having five to fourteen members. One having ordinary skill in the art will recognize that the maximum number of heteroatoms in a stable, chemically feasible heteroaryl ring is determined by the size of the ring and valence. In general, a heteroaryl ring may have one to four heteroatoms so long as the heteroaryl ring is chemically feasible and stable. The term "heteroaralkyl" refers to a heteroaryl group comprising a ($C_1$-$C_3$) alkyl group, wherein the alkyl group links the heteroaralkyl group to the remainder of the molecule. The term heteroaryl includes heteroaralkyl ring systems unless otherwise indicated. Heteroaryl groups include, without limitation, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, or 3-thienyl. The term "heteroaryl ring" or "heteroaryl group" also refers to rings that are optionally substituted, unless otherwise indicated.

Examples of fused polycyclic heteroaryl and aryl ring systems in which a carbocyclic aromatic ring or heteroaryl ring is fused to one or more other rings include, without limitation, tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl" and "heteroaryl", as it is used herein, is a group in which one or more aryl rings and/or heteroaryl rings are fused to a non-aromatic cycloalkyl or heterocyclic ring, for example, indanyl or tetrahydrobenzopyranyl.

Suitable substituents on the unsaturated carbon atom of an aryl, heteroaryl, aralkyl, or heteroaralkyl group are selected from halogen; haloalkyl; —$CF_3$; —$R^7$; —$OR^7$; —$SR^7$, 1,2-methylene-dioxy; 1,2-ethylenedioxy; protected OH (such as acyloxy); phenyl (Ph); Ph substituted with $R^7$; —O(Ph); —O(Ph) substituted with $R^7$; —$CH_2$(Ph); —$CH_2$(Ph) substituted with $R^7$; —$CH_2CH_2$(Ph); —$CH_2CH_2$(Ph) substituted with $R^7$; —$NO_2$; —CN; —$N(R^7)_2$; —$NR^7C(O)R^7$; —$NR^7C(O)N(R^7)_2$; —$NR^7CO_2R^7$; —$NR^7NR^7C(O)R^7$; —$NR^7NR^7C(O)N(R^7)_2$; —$NR^7NR^7CO_2R^7$; —C(O)C(O)$R^7$; —C(O)$CH_2$C(O)$R^7$; —$CO_2R^7$, —C(O)$R^7$; —C(O)N($R^7$)$_2$; —OC(O)N($R^7$)$_2$; —S(O)$_2R^7$; —$SO_2$N($R^7$)$_2$; —S(O)$R^7$; —$NR^7SO_2$N($R^7$)$_2$; —$NR_7SO_2R^7$; —C(=S)N($R^7$)$_2$; —C(=NH)—N($R^7$)$_2$; —($CH_2$)$_y$NHC(O)$R^7$; —($CH_2$)$_yR^7$; —($CH_2$)$_y$NHC(O)NH$R^7$; —($CH_2$)$_y$NHC(O)O$R^7$; —($CH_2$)$_y$NHS(O)$R^7$; —($CH_2$)$_y$NHSO$_2R^7$; —($CH_2$)$_y$NHC(O)CH(V$_z$—$R^7$)($R^7$); wherein each $R^7$ is independently selected from H, optionally substituted $C_{1-6}$ aliphatic, an unsubstituted 5-10 membered heteroaryl or heterocyclic ring, phenyl (Ph), —O(Ph), or —$CH_2$(Ph); wherein y is 0-6; z is 0-1; and V is a linker group. When $R^7$ is $C_{1-6}$ aliphatic, it may be substituted with one or more substituents selected from —$NH_2$, —NH($C_{1-4}$ aliphatic), —N($C_{1-4}$ aliphatic)$_2$, —S(O) ($C_{1-4}$ aliphatic), —$SO_2$($C_{1-4}$ aliphatic), halogen, —$C_{1-4}$ aliphatic, —OH, —O—($C_{1-4}$ aliphatic), nitro, cyano, —$CO_2$H, —$CO_2$($C_{1-4}$ aliphatic), —O(halo $C_{1-4}$ aliphatic), or -halo ($C_{1-4}$ aliphatic); wherein each $C_{1-4}$ aliphatic is unsubstituted.

An aliphatic group, a carbocyclic ring or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNH$R^8$, =NN($R^8$)$_2$, =N—, O$R^8$, =NNHC(O)$R^8$, =NNHCO$_2$ (alkyl), =NNHSO$_2$(alkyl), or =N$R^8$, where each $R^8$ is independently selected from hydrogen, or an optionally substituted $C_{1-6}$ aliphatic group. When $R^8$ is $C_{1-6}$ aliphatic, it may be substituted with one or more substituents selected from amino, halogen, nitro, cyano, carboxy, t-butoxy, methoxy, ethoxy, hydroxy, or $CF_3$.

Substituents on the nitrogen of a non-aromatic heterocyclic ring are selected from —$R^9$, —N($R^9$)$_2$, —C(O)$R^9$, —$CO_2R_9$, —C(O)C(O)$R^9$, —C(O)$CH_2$C(O)$R^9$, —$SO_2R^9$, —$SO_2$N($R^9$)$_2$, —C(=S)N($R^9$)$_2$, —C(=NH)—N($R^9$)$_2$, and —$NR^9SO_2R^9$; wherein each $R^9$ is independently selected from H, an optionally substituted $C_{1-6}$ aliphatic, optionally substituted phenyl (Ph), optionally substituted —O(Ph), optionally substituted —$CH_2$ (Ph), optionally substituted —$CH_2CH_2$(Ph), or an unsubstituted 5-6 membered heteroaryl or heterocyclic ring. When $R^9$ is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), nitro, cyano, —$CO_2$H, —$CO_2$ ($C_{1-4}$ aliphatic), —O(halo $C_{1-4}$ aliphatic), or -halo($C_{1-4}$ aliphatic), wherein each $C_{1-4}$ aliphatic is unsubstituted.

The term "linker group" or "linker" means an organic moiety that connects two parts of a compound. Linkers are comprised of —O—, —S—, —NR*—, —C(R*)$_2$—, —C(O)—, or an alkylidene chain. The alkylidene chain is a saturated or unsaturated, straight or branched, $C_{1-6}$ carbon chain which is optionally substituted, and wherein up to two non-adjacent saturated carbons of the chain are optionally replaced by —C(O)—, —C(O)C(O)—, —C(O)NR*—, —C(O)NR*NR*—, —$CO_2$—, —OC(O)—, —NR*$CO_2$—, —O—, —NR*C(O)NR*—, —OC(O)NR*—, —NR*NR*—, —NR*C(O)—, —S—, —SO—, —$SO_2$—, —NR*—, —$SO_2$NR*—, or —NR*$SO_2$—; wherein R* is selected from hydrogen or aliphatic. Optional substituents on the alkylidene chain are as described above for an aliphatic group.

The term "patient" includes human and mammalian veterinary subjects.

One object of the instant invention is to provide compounds having the general formulae:

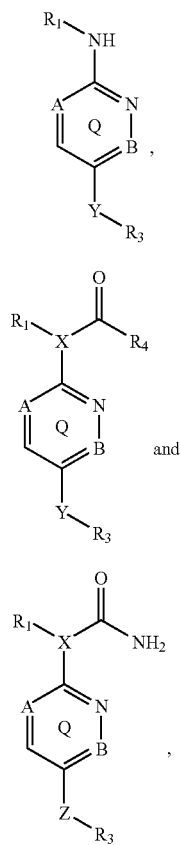

or a pharmaceutically acceptable derivative thereof, wherein:

A is N or CR.

B is N or CR.

X is N or CH.

Y is C(O), CHOH, $CH_2$, S, S(O), $S(O)_2$, NH, NR, O or Z.

Z is CHOH, —[($C_2$-$C_3$)-alkyl]-, —S—[($C_1$-$C_3$)-alkyl]-, —O—[($C_1$-$C_3$)-alkyl]-, —NH—[($C_1$-$C_3$)-alkyl]-, —[($C_2$-$C_3$)-alkenyl]-, —[($C_2$-$C_3$)-alkynyl]-, —O—[($C_2$-$C_3$)-alkenyl]-, —O—[($C_2$-$C_3$)-alkynyl]-, —S—[($C_2$-$C_3$)-alkenyl]-, —S—[($C_2$-$C_3$)-alkynyl]-, —NH—[($C_2$-$C_3$)-alkenyl]-, —NH—[($C_2$-$C_3$)-alkynyl]-, —[($C_1$-$C_3$)-alkyl]-S—, —[($C_1$-$C_3$)-alkyl]-O—, —[($C_1$-$C_3$)-alkyl]-NH—, —[($C_2$-$C_3$)-alkenyl]-O—, —[($C_2$-$C_3$)-alkynyl]-O—, —[($C_2$-$C_3$)-alkenyl]-S—, —[($C_2$-$C_3$)-alkynyl]-S—, —[($C_2$-$C_3$)-alkenyl]-NH— or —[($C_2$-$C_3$)-alkynyl]-NH—.

The carbon atoms of Q may be optionally substituted with R.

$R_1$ is selected from aryl, heteroaryl, carbocyclyl, heterocyclyl or $C_{1-10}$ aliphatic, any of which may be optionally substituted.

$R_3$ is selected from aryl, heteroaryl, carbocyclyl, heterocyclyl, or $C_{1-10}$ aliphatic, any of which may be optionally substituted.

$R_4$ is selected from $NHR_5$, $N(R_5)_2$, $OR_5$, $C(O)OR_5$, —$C(O)R_5$ or $R_6$.

Each $R_5$ is independently selected from aryl, heteroaryl, carbocyclyl, heterocyclyl or $C_{1-5}$ aliphatic;

$R_6$ is selected from aryl, heteroaryl, carbocyclyl, heterocyclyl or $C_{1-5}$ aliphatic, any of which may be optionally substituted.

Each R is independently selected from H, halo or a straight or branched chain $C_1$-$C_4$ alkyl.

Each of $R_1$, $R_5$ and $R_6$ are independently and optionally substituted with up to 4 substituents, each of which is independently selected from halo; $C_1$-$C_3$ alkyl optionally substituted with $NR'_2$, OR', $CO_2R'$ or $CONR'_2$; O—($C_1$-$C_3$)-alkyl optionally substituted with $NR'_2$, OR', $CO_2R'$ or $CONR'_2$; R'; $NR'_2$; $OCF_3$; $CF_3$; $NO_2$; $CO_2R'$; CONR'; SR'; COR'; $S(O_2)N(R')_2$; $SCF_3$; CN; N(R')C(O)R'; N(R')C(O)OR'; N(R')C(O)C(O)R'; N(R')S($O_2$)R'; OR'; OC(O)R'; $OP(O)_3H_2$; or N=C—N(R')$_2$.

$R_3$ is optionally substituted with up to 4 substituents, each of which is independently selected from halo; $C_1$-$C_3$ straight or branched alkyl optionally substituted with N(R')$_2$, OR', $CO_2R'$, $S(O_2)N(R')_2$, N=C—N(R')$_2$, R', or CON(R')$_2$; O—($C_1$-$C_3$)-alkyl optionally substituted with N(R')$_2$, OR', $CO_2R'$, $S(O_2)N(R')_2$, N=C—N(R')$_2$, R', or CON(R')$_2$; N(R')$_2$; $OCF_3$; $CF_3$; $NO_2$; CON(R')$_2$; R'; OR'; SR'; COR'; C(O)OR'; $S(O_2)N(R')_2$; $SCF_3$; N=C—N(R')$_2$; or CN.

R' is selected from hydrogen; ($C_1$-$C_3$)-alkyl; ($C_2$-$C_3$)-alkenyl or alkynyl; a 5-8 membered aryl ring system, a 5-8 membered heteroaryl ring system or a 5-6 membered heterocyclic ring system, any of which may be independently and optionally substituted with 1 to 3 substituents independently selected from halo, methoxy, cyano, nitro, amino, hydroxy, methyl or ethyl.

Provided that in compounds of Formula I, when A is C, B is N, Y is CHOH, O, S, $CH_2$ or NH, and $R_3$ is an N-containing heteroaryl, then $R_1$ is not aryl, carbocyclyl or pyridyl;

when A is N, B is C, Y is C=O and $R_3$ is a $C_1$-$C_8$ alkyl, $C_6$-$C_{12}$ aryl or $C_7$-$C_{12}$ aralkyl, then $R_1$ is not 1-pyrroline or 1-indole; or when A and B are both C, Y is CHOH or $CH_2$, and $R_3$ is a substituted phenyl, then $R_1$ is not cyclopropyl or benzyl.

Further provided that in compounds of Formula II, when X is N, A and B are both C, Y is $CH_2$ or O, $R_3$ is a $C_{1-5}$ aliphatic, $R_4$ is $NHR_5$, $N(R_5)_2$, or a $C_{1-4}$ aliphatic substituted with a substituted or unsubstituted piperadine or piperazine; then $R_1$ is not $CH_3$ or a ring system comprising a six-membered heteroaryl; or in compounds of Formulae I and II, when X, if present, is N, A and B are both C, Y is $CH_2$, $R_1$ is a $C_{1-8}$ aliphatic or is phenyl, $R_4$, if present, is a $C_{1-6}$ aliphatic or is phenyl, and $R_3$ is a substituted $C_5$ alkyl or is methylene substituted with 4-hydroxy-tetrahydro-pyran-2-one, then Q is not simultaneously substituted with (a) a $C_{6-10}$ optionally substituted aryl, (b) $C_{1-10}$ aliphatic or carbocyclyl, and (c) a substituted $C_6$ alkyl or alkene, ethyl or ethylene substituted with 4-hydroxy-tetrahydro-pyran-2-one, $CH_2O$ subsituted with H, $C_{1-10}$ aliphatic, halo, phenyl, $C_{6-10}$ aryl or a carbonyl substituted with $C_{1-8}$ aliphatic or phenyl.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

In a preferred embodiment of the invention, either A or B are C. In a more preferred embodiment, both A and B are C. In another preferred embodiment, $R_1$ is aryl or heteroaryl. In yet another preferred embodiment of formulae I and II, Y is C(O). In another preferred embodiment of formulae II and III, X is N.

A more preferred embodiment of the invention is shown in formula Ia:

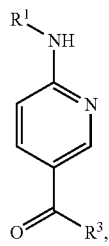

(Ia)

wherein $R_1$ and $R_3$ are defined above. In an even more preferred embodiment, $R_1$ is selected from phenyl or pyridyl containing 1 to 3 substituents, and $R_3$ is selected from phenyl, thienyl or pyridyl containing 0 to 3 substituents.

Another more preferred embodiment of the invention is shown in formula IIa:

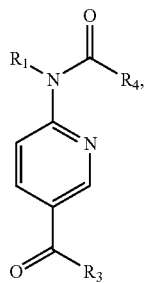

(IIa)

wherein $R_1$ and $R_3$ are defined above. In an even more preferred embodiment, $R_1$ is selected from phenyl or pyridyl containing 1 to 3 substituents, and $R_3$ is selected from phenyl, thienyl or pyridyl containing 0 to 3 substituents.

According to another preferred embodiment of the invention, $R_1$ is selected from phenyl or pyridyl containing 1 to 3 substituents. More preferably, said substituents are independently selected from chloro, fluoro, bromo, —$CH_3$, —$OCH_3$, —OH, —$CF_3$, —$OCF_3$, —$O(CH_2)_2CH_3$, $NH_2$, 3,4-methylenedioxy, —$N(CH_3)_2$, —NH—$S(O)_2$-phenyl, —NH—C(O)O—$CH_2$-4-pyridine, —NH—C(O)$CH_2$-morpholine, —NH—C(O)$CH_2$—$N(CH_3)_2$, —NH—C(O)$CH_2$-piperazine, —NH—C(O)$CH_2$-pyrrolidine, —NH—C(O)C(O)-morpholine, —NH—C(O)C(O)-piperazine, —NH—C(O)C(O)-pyrrolidine, —O—C(O)$CH_2$—$N(CH_3)_2$, or —O—$(CH_2)_2$—$N(CH_3)_2$. Even more preferably, at least one of said substituents is in the ortho position.

Even more preferred for $R_1$ are phenyl or pyridyl containing at least 2 of the above-indicated substituents both being in the ortho position.

According to a preferred embodiment, $R_3$ is aliphatic, phenyl, pyridyl, thienyl or naphthyl and optionally contains up to 3 substituents, each of which is independently selected from chloro, fluoro, bromo, methyl, ethyl, isopropyl, —$OCH_3$, —OH, —$NH_2$, —$CF_3$, —$OCF_3$, —$SCH_3$, —$OCH_3$, —C(O)OH, —C(O)$OCH_3$, —$CH_2NH_2$, —$N(CH_3)_2$, pyrrolyl, —$CH_2$-pyrrolidine and —$CH_2OH$.

Some specific examples of preferred $R_3$ are: n-butyl, isobutyl, unsubstituted phenyl,

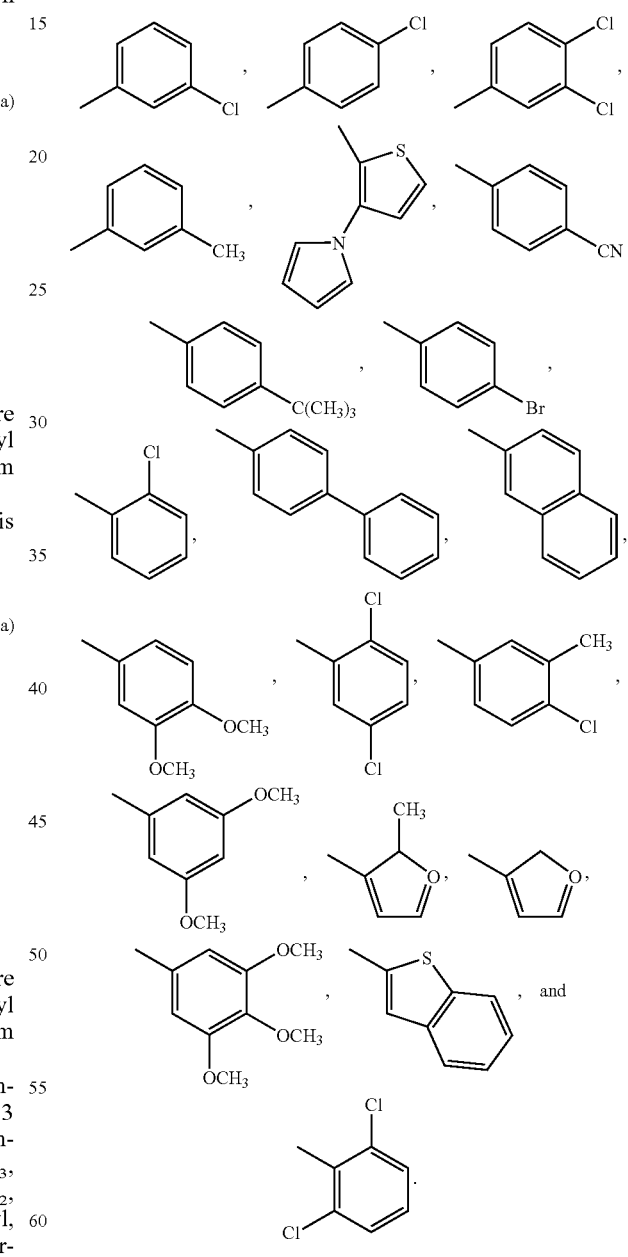

According to another preferred embodiment of the invention, $R_4$, if present, is selected from phenyl, —$C(CH_3)_3$, —$CH_2OCH_3$, —$CH_3$, 4-bromophenyl, cyclohexane, —$CH_2CH_2C(O)OCH_3$, 3-trifluoromethylphenyl, 3-trifluoromethyl-4-fluorophenyl, —C(O)$OCH_2CH_3$, —$CH_2CH$ (CH₃)₂, —CH₂CH₂-phenyl, —CH₂-4-fluorophenyl, —OCH₂-phenyl, —O-4fluorophenyl,
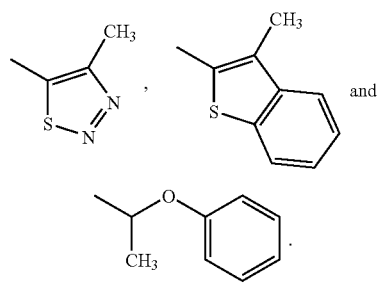, and
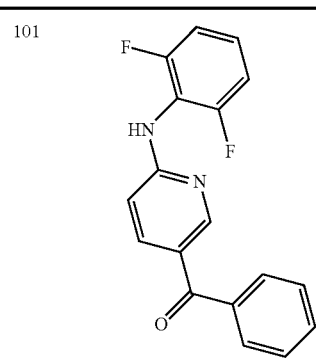.
Some preferred embodiments are provided in Tables 1-6 below:
TABLE 1
| Cpd. No. | Structure |
|---|---|
| 101 | 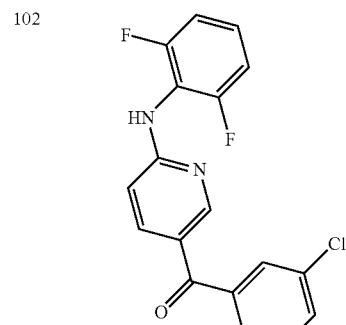 |
| 102 | 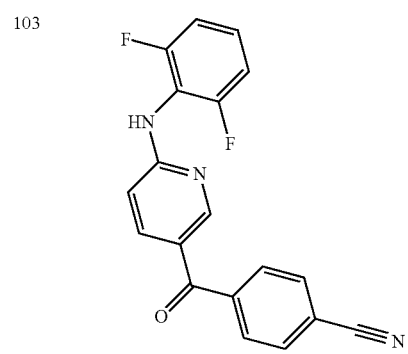 |
| 103 | 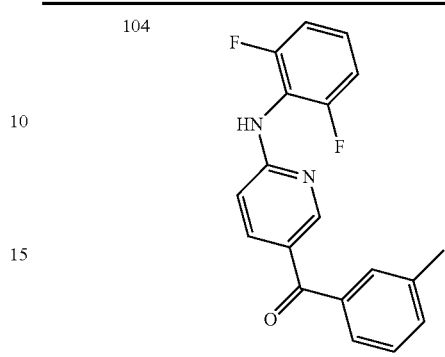 |
TABLE 1-continued
| Cpd. No. | Structure |
|---|---|
| 104 | 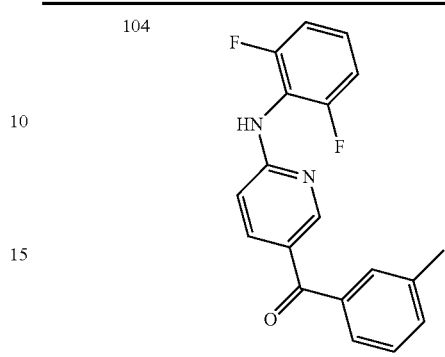 |
| 105 | 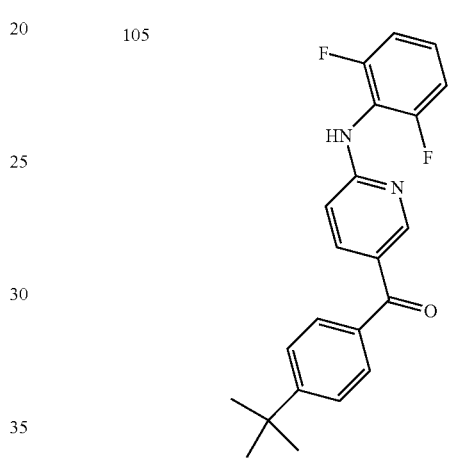 |
| 106 | 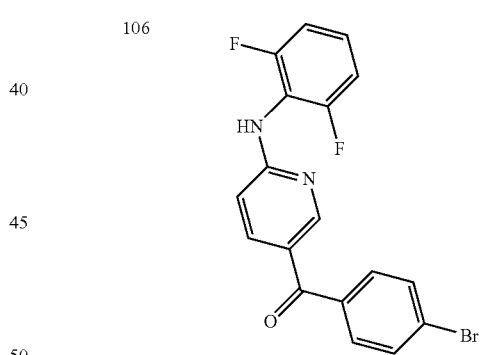 |
| 107 | 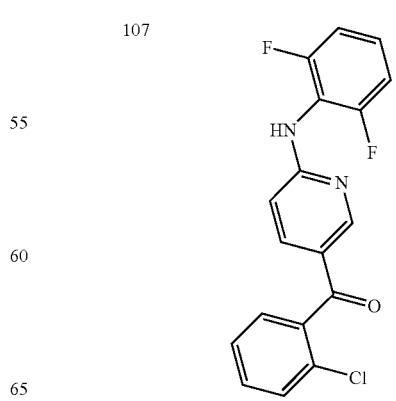 |

TABLE 1-continued
| Cpd. No. | Structure |
|---|---|
| 108 | 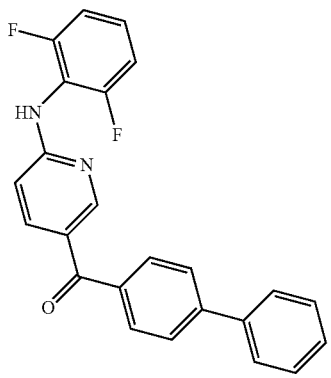 |
| 109 | 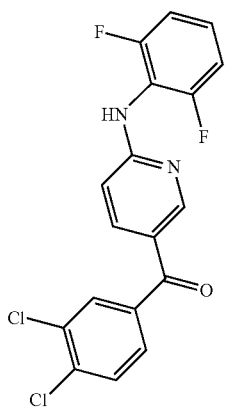 |
| 110 | 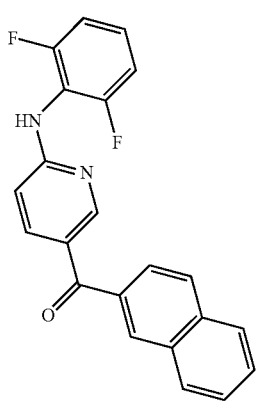 |
| 111 | 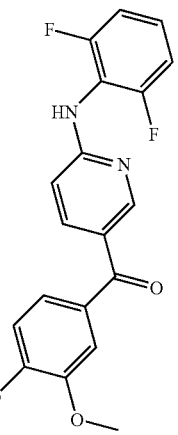 |
| 112 | 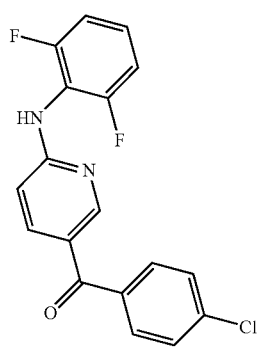 |
| 113 | 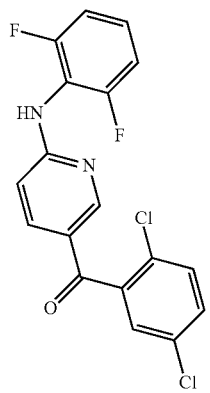 |
| 114 | 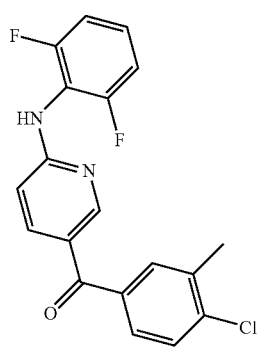 |

TABLE 1-continued
| Cpd. No. | Structure |
|---|---|
| 115 | 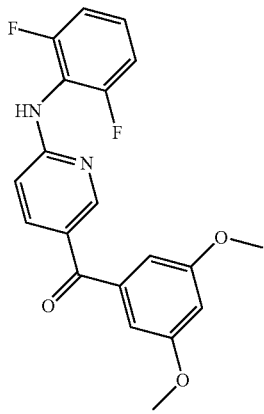 |
| 116 | 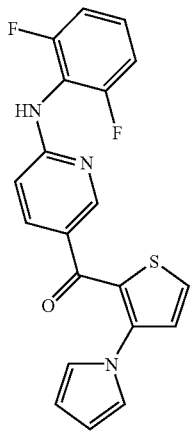 |
| 117 | 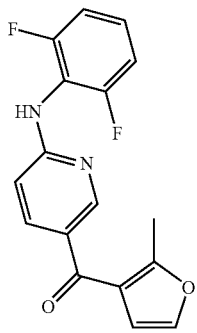 |
| 118 | 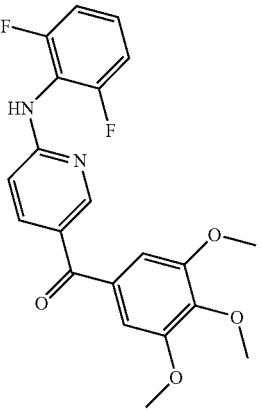 |
| 119 | 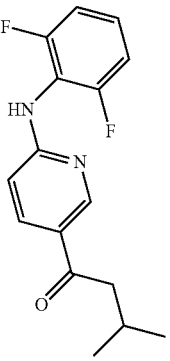 |
| 120 | 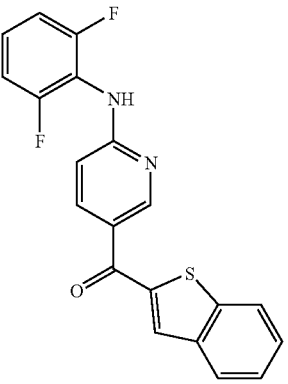 |

TABLE 2

| Cpd. No. | Structure |
|---|---|
| 201 | (2,6-difluorophenyl)amino-pyridine with phenyl(hydroxy)methyl |

TABLE 3

| Cpd. No. | Structure |
|---|---|
| 301 | 2-[3,5-bis(trifluoromethyl)phenyl]-2-[6-(furan-2-ylmethylthio)pyridazin-3-yl]acetamide |

TABLE 4

| Cpd. No. | Structure |
|---|---|
| 401 | 2-[(2,6-difluorophenyl)amino]-5-butylpyridine |

TABLE 4-continued

| Cpd. No. | Structure |
|---|---|
| 402 | N-(2,6-difluorophenyl)-N-[5-(3-(2,6-dichlorophenoxy)prop-1-yn-1-yl)pyridin-2-yl]urea |

TABLE 5

| Cpd. No. | Structure |
|---|---|
| 501 | 2-[(2,6-difluorophenyl)amino]-5-(phenylsulfinyl)pyridine |
| 502 | 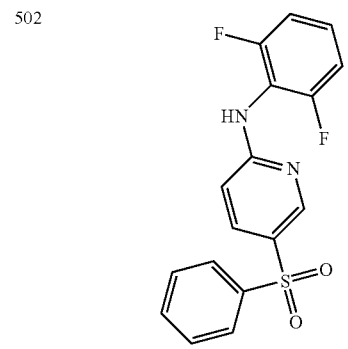 2-[(2,6-difluorophenyl)amino]-5-(phenylsulfonyl)pyridine |

TABLE 5-continued
| Cpd. No. | Structure |
|---|---|
| 503 | 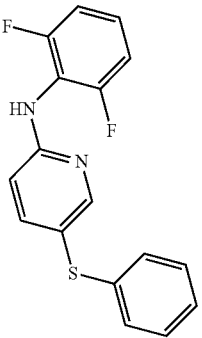 |
TABLE 6
| Cpd. No. | Structure |
|---|---|
| 601 | 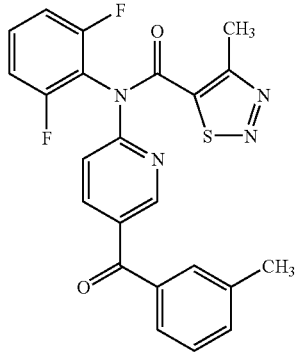 |
| 602 | 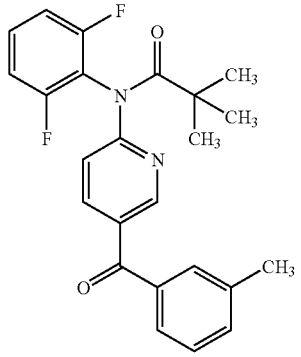 |
TABLE 6-continued
| Cpd. No. | Structure |
|---|---|
| 603 | 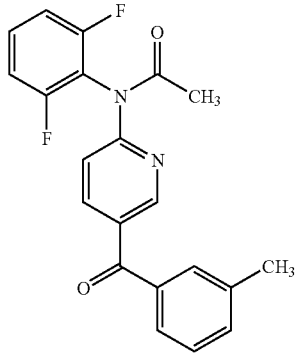 |
| 604 | 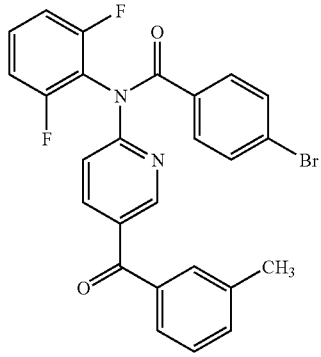 |
| 605 | 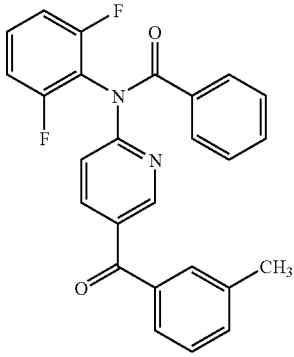 |
| 606 | 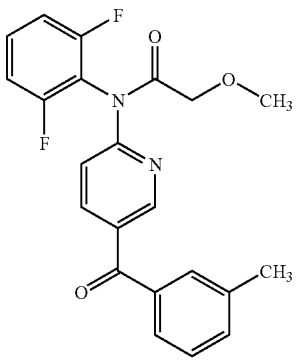 |

TABLE 6-continued

| Cpd. No. | Structure |
|---|---|
| 607 | 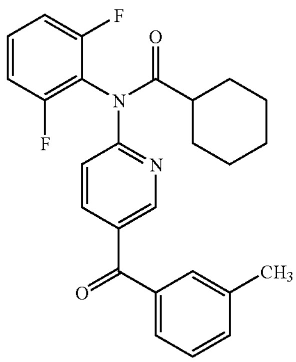 |
| 608 | 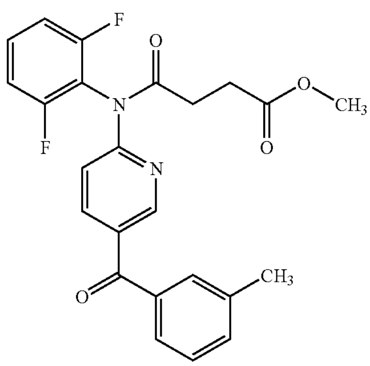 |
| 609 | 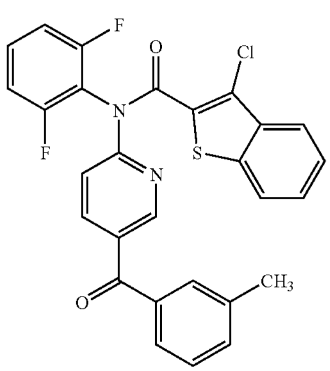 |
| 610 | 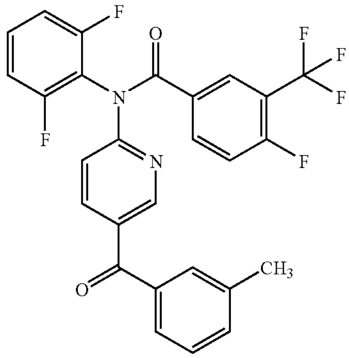 |
| 611 | |
| 612 | |
| 613 | |
| 614 | |

TABLE 6-continued
| Cpd. No. | Structure |
|---|---|
| 615 | 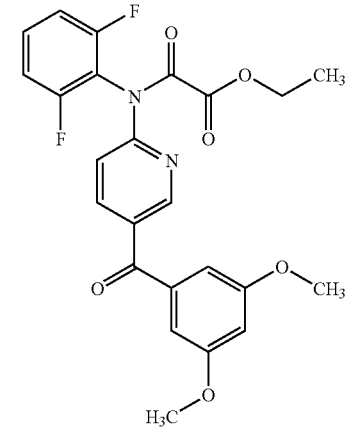 |
| 616 | 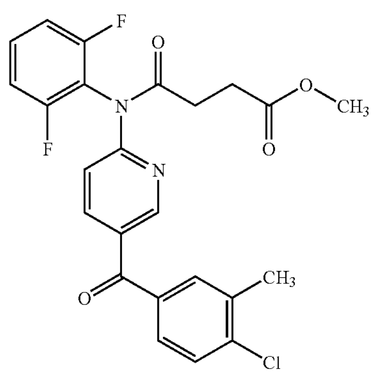 |
| 617 | 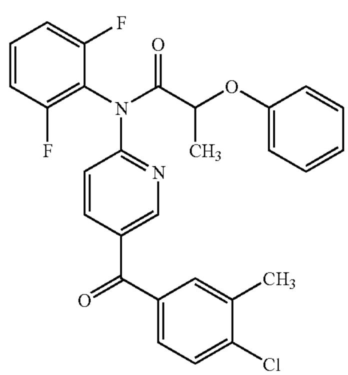 |
| 618 | |用
TABLE 6-continued
| Cpd. No. | Structure |
|---|---|
| 619 | 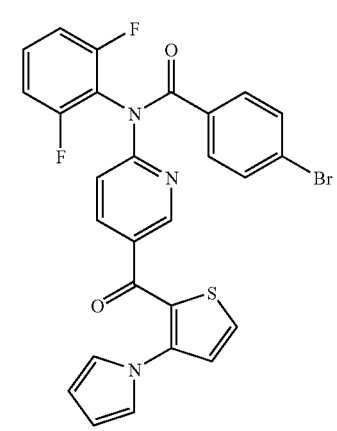 |
| 620 | 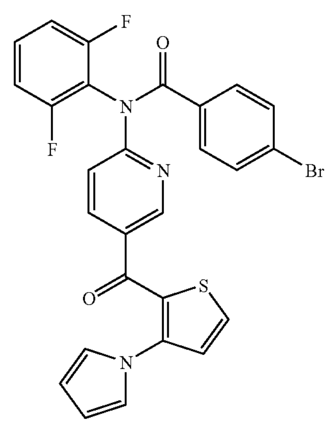 |
| 621 | 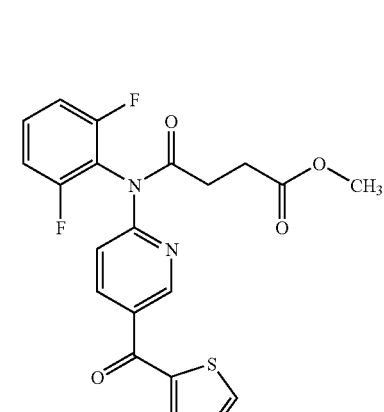 |

TABLE 6-continued
| Cpd. No. | Structure |
|---|---|
| 622 | 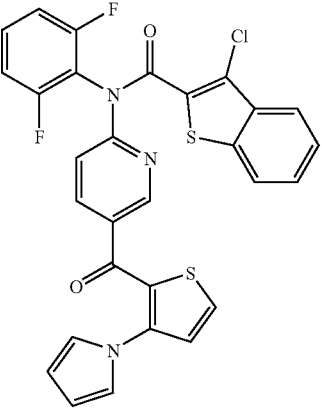 |
| 623 | 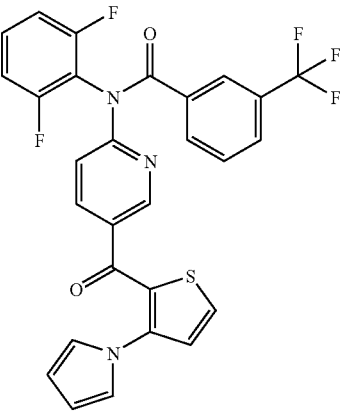 |
| 624 | 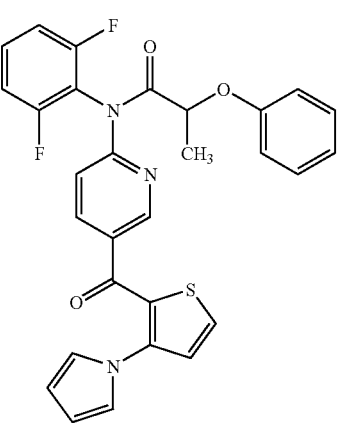 |
| 625 | 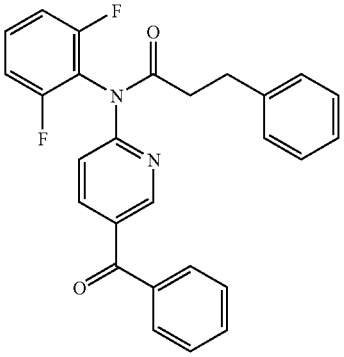 |
| 626 | 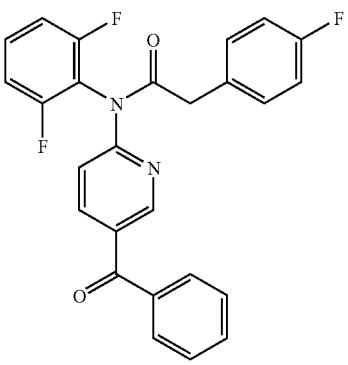 |
| 627 | 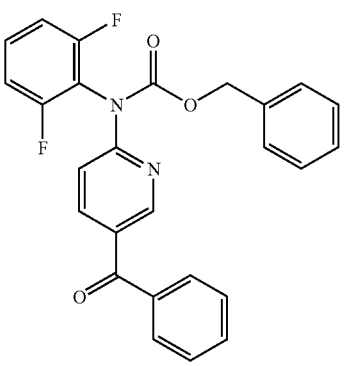 |
| 628 | 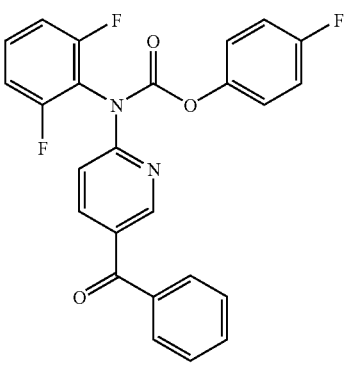 |

TABLE 6-continued

| Cpd. No. | Structure |
|---|---|
| 629 | (structure) |
| 630 | (structure) |
| 631 | (structure) |
| 632 | (structure) |
| 633 | (structure) |
| 634 | (structure) |
| 635 | (structure) |

According to another embodiment, the present invention provides methods of producing the above-identified compounds. Representative synthesis schemes are depicted in Examples 1-9 below.

According to another embodiment of the invention, the activity of the p38 inhibitors of this invention may be assayed in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands.

Cell culture assays of the inhibitory effect of the compounds of this invention may determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention are the suppression of hind paw edema in rats with *Mycobacterium butyricum*-induced adjuvant arthritis. This is described in J. C. Boehm et al., J. Med. Chem., 39, pp. 3929-37 (1996), the disclosure of which is herein incorporated by reference. The p38 inhibitors of this invention may also be assayed in animal models of arthritis, bone resorption, endotoxin shock and immune function, as described in A. M. Badger et al., J. Pharmacol. Experimental Therapeutics, 279, pp. 1453-61 (1996), the disclosure of which is herein incorporated by reference.

The p38 inhibitors or pharmaceutical salts thereof may be formulated into pharmaceutical compositions for administration to animals or humans. These pharmaceutical compositions, which comprise an amount of p38 inhibitor effective to treat or prevent a p38-mediated condition and a pharmaceutically acceptable carrier, are another embodiment of the present invention.

The term "p38-mediated condition", as used herein means any disease or other deleterious condition in which p38 is known to play a role. This includes conditions known to be caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, and multiple myeloma.

Angiogenic disorders which may be treated or prevented by the compounds of this invention include solid tumors, ocular neovasculization, infantile haemangiomas.

Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, cerebral ischemias or neurodegenerative disease caused by traumatic injury.

"p38-mediated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors of the instant invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" which may be treated by the compounds of this invention include edema, analgesia, fever and pain, such as neuromuscular pain, headache, cancer pain, dental pain and arthritis pain.

The diseases that may be treated or prevented by the p38 inhibitors of this invention may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated disease or condition includes, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated disease or condition includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this invention may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N—($C_{1-4}$ alkyl)$4^+$ salts. This invention also envisions the quaternization of any basic nitrogen-containing groups of the compounds disclosed herein. Water or oil-soluble or dispersible products may be obtained by such quaternization.

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

Preferred salts include salts formed from hydrochloric, sulfuric, acetic, succinic, citric and ascorbic acids.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of p38 inhibitor that may be combined with the carrier materials to produce a single dosage form will vary depending upon the host treated and the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, angiogenic disorders, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition, may be administered together with the inhibitors of this invention.

For example, chemotherapeutic agents or other anti-proliferative agents may be combined with the p38 inhibitors of this invention to treat proliferative diseases.

Those additional agents may be administered separately, as part of a multiple dosage regimen, from the p38 inhibitor-containing composition. Alternatively, those agents may be part of a single dosage form, mixed together with the p38 inhibitor in a single composition.

In order that the invention described herein may be more fully understood, the following examples are set forth. It should be understood that these examples are for illustrative purposes only and are not to be construed as limiting this invention in any manner.

EXAMPLE 1

Synthesis of
[6-(2,6-Difluorophenylamino)-pyridin-3-yl]
Arylmethanones

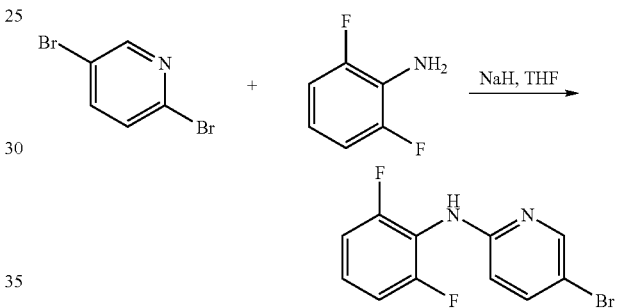

To stirred suspension of sodium hydride (1.9 equivalents [eq.]) in tetrahydrofuran (THF) (10 ml/g) at room temperature was added dropwise a solution of 2,6-difluoroaniline (1.5 eq.) in THF (8 ml/g). The resultant mixture was stirred at room temperature for 30 minutes. A solution of 2,5-dibromopyridine (1.0 eq.) in THF (8 ml/g) was added and the resultant mixture was stirred at room temperature for 10 minutes prior to being heated to 65° C. overnight. The reaction was cooled, quenched with water and extracted with 3 portions of diethyl ether. The combined organic extracts were dried over MgSO$_4$ and concentrated in vacuo to give the desired product. No further purification was required.

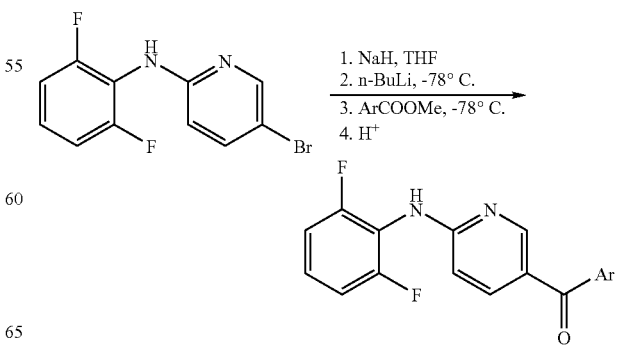

To a stirred solution of sodium hydride (2 eq.) in rigorously degassed THF (approximately 20 mL/g) at 0° C. was added dropwise a solution of (5-Bromopyridin-2-yl)-(2,6-difluorophenyl)-amine in THF (approximately 10 mL/g). The solution was allowed to warm slowly to room temperature over 1 hour, after which time the solution was cooled to −78° C. n-Butyllithium (approximately 1.6 M in hexanes, 1.1 eq.) was added dropwise over 15 minutes and the resultant solution was stirred at −78° C. for 1 hour. The 'dianion' solution was then added via a cooled cannula to a solution of the appropriate methoxy arylcarbonyl (1.1 eq.) in THF (approximately 10 mL/g) at −78° C. After stirring at −78° C. for at least 5 hours, the reaction was quenched with a methanolic solution of ammonium chloride at −78° C. and allowed to warm slowly to room temperature. The solution was partitioned between ethyl acetate and water (equal volumes, using approximately 25 mL/g of 2-(2,6-difluoro)aniline-5-bromo-pyridine used). The organic layer was removed and the aqueous layer re-extracted with ethyl acetate (approximately 25 mL/g). The combined organic layer was washed with saturated aqueous brine solution (approximately 25 mL/g), dried over $MgSO_4$ and concentrated in vacuo to give the crude reaction product, which was typically purified by column chromatography, using various ratios of ethyl acetate:hexane as eluant.

One having ordinary skill in the art may synthesize other arylmethanones following the teachings of the specification. For instance, one may use other than (2,6-difluorophenyl)-amine to prepare compounds having a different $R_1$. Further, one may use heteroarylmethanones to synthesize compounds of this invention having a heteroaryl for $R_1$.

EXAMPLE 2

Synthesis of 2-(2,6-Difluoro)Aniline-5-Alkyl-Pyridines

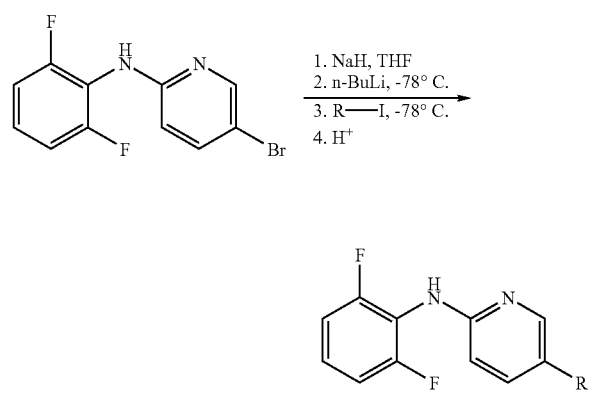

The compounds were produced as for the arylketones shown above in Scheme 1, except that an alkyl iodide (1.1 eq.) was employed as the electrophile, and was added directly to the 'dianion' solution. The reactions did not require low temperature quenching and were allowed to warm to room temperature overnight, before work-up. One having ordinary skill in the art may synthesize other alkylketones following the teachings of the instant specification.

EXAMPLE 3

Synthesis of 2-(2,6-Difluoro)Aniline-5-Arylsulfenyl/Arylsulfinyl/Arylsulfonyl-Pyridines

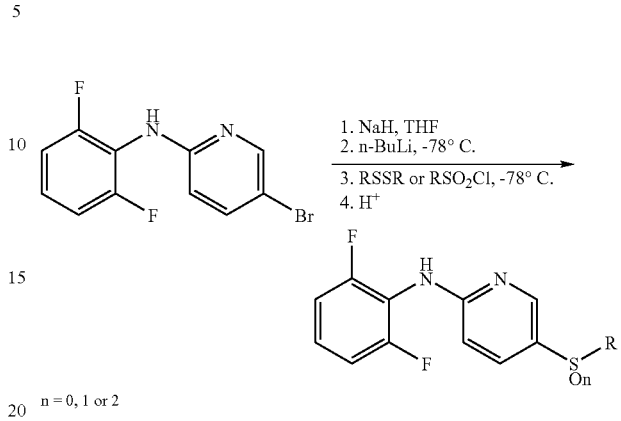

n = 0, 1 or 2

The compounds were produced as for the arylketones shown above in Scheme 1, except that an appropriate sulfur electrophile (a diaryldisulfide for sulfenyl-pyridines or an arylsulfonyl halide for sulfonyl-pyridines) (1.1 eq.) was employed as the electrophile, and was added directly to the 'dianion' solution. The reactions were quenched with a methanolic solution of ammonium chloride at −78° C., before work-up. Sulfinyl-pyridines were synthesized by oxidizing the corresponding sulfenyl-pyridines at 0° C. using meta-chloroperbenzoic acid (m-CPBA; 1.1 eq. of approximately 50% w/w). One having ordinary skill in the art may synthesize other arylsulfenyl, arylsulfinyl and arylsulfonyl pyridines or heteroarylsulfenyl, heteroarylsulfinyl or heteroarylsulfonyl pyridines following the teachings of the specification.

EXAMPLE 4

Part A: Synthesis of (2,6-Difluoro-phenyl)-(5-iodo-pyridin-2-yl)-amine

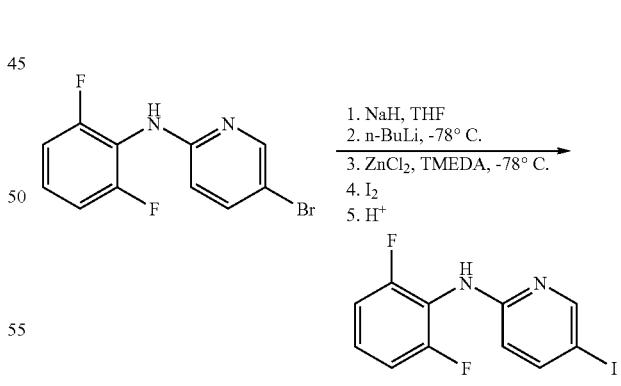

To a stirred solution of sodium hydride (2 eq.) in rigorously degassed THF (approximately 50 mL/g) at 0° C., was added dropwise a solution of (2,6-difluorophenyl)-(5-bromopyridin-2-yl)-amine (1 eq.) in THF (approximately 15 mL/g). The solution was allowed to warm slowly to room temperature over 1 hour, after which time the solution was cooled to −78° C. n-Butyllithium (approximately 1.6 M in hexanes, 1.1 eq.) was added dropwise over 15 minutes and the resultant solution was stirred at −78° C. for 1 hour. Zinc chloride/TMEDA complex (prepared as described by Isobe et al., Chem. Lett., 1977, 679) was added as a solid in a single portion and the solution was allowed to warm to 0° C. over 30 minutes, and was stirred at 0° C. for a further 1 hour. A solution of iodine (1.1 eq.) in THF (approximately 10 mL/g) was added and the solution was allowed to warm to room temperature. After stirring at room temperature for at least 1 hour, the reaction was quenched with a saturated aqueous solution of ammonium chloride. The solution was extracted with diethyl ether (3 times approximately 50 mL/g of 5-Bromopyridin-2-yl)-(2,6-difluorophenyl)-amine used). The combined organic layer was washed successively with 10% aqueous sodium sulfite solution (approximately 50 mL/g), saturated aqueous sodium thiosulfate solution (approximately 50 mL/g) and water (approximately 50 mL/g), dried over MgSO$_4$ and concentrated in vacuo to give the crude reaction product as an orange oil. Purification by column chromatography, using 10% ethyl acetate:hexane as eluant, provided (2,6-Difluoro-phenyl)-(5-iodo-pyridin-2-yl)-amine (Rf 0.22) in approximately 50% yield.

Part B: Synthesis of (2,6-Difluoro-phenyl)-(5-vinyl-pyridin-2-yl)-amine

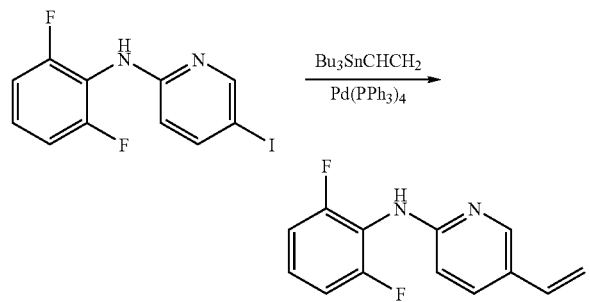

To a mixture of (2,6-Difluoro-phenyl)-(5-iodo-pyridin-2-yl)-amine and Pd(PPh3)$_4$ (approximately 10 mol %) in toluene (approximately. 80 mL/g) at room temperature was added tributylvinyltin (1.1 eq.). The reaction was placed under a N$_2$ atmosphere and heated to 80° C. overnight. The solution was cooled, diluted with ethyl acetate (approximately 80 mL/g) and filtered through a pad of celite. The celite was washed with a further portion of ethyl acetate. The organic layer was dried over MgSO$_4$ and concentrated in vacuo to give the crude reaction product as a yellow oil. Purification by column chromatography, using 10% ethyl acetate:hexane as eluant provided (2,6-Difluoro-phenyl)-(5-vinyl-pyridin-2-yl)-amine (Rf 0.14) in 66% yield.

Part C: Synthesis of (2,6-Difluorophenyl)-(5-alkynyl-pyridin-2-yl)-amine

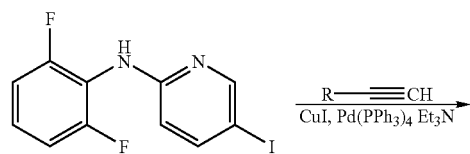

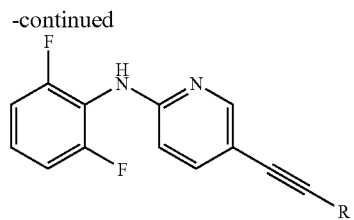

To a mixture of copper (I) iodide (approximately 5 mol %) and PdCl$_2$(PPh$_3$)$_2$ (approximately 5 mol %) was added a solution of 2-(2,6-difluoro)aniline-5-iodo-pyridine in triethylamine (approximately 25 mL/g) at room temperature. The reaction was placed under a N$_2$ atmosphere and the appropriate alkyne (1.1 eq.) added dropwise. The reaction was stirred at room temperature or 50° C. (dependent on the alkyne) overnight. The solution was cooled, poured onto 10% aqueous hydrochloric acid (approximately 250 mL/g of 2-(2,6-difluoro)aniline-5-iodo-pyridine used). The aqueous layer was extracted with diethyl ether (2 times approximately 500 mL/g), and the organic layer washed with saturated aqueous brine solution (approximately 500 mL/g). The organic layer was dried over MgSO$_4$ and concentrated in vacuo to give the crude reaction product, which was purified by column chromatography, using various ratios of ethyl acetate:hexane as eluant. One having ordinary skill in the art may synthesize other alkynyl pyridinyl amines following the teachings of the instant specification.

EXAMPLE 6

Part A: Synthesis of (6-Chloropyridazin-3-yl)-(2,6-difluorophenyl)-acetonitrile

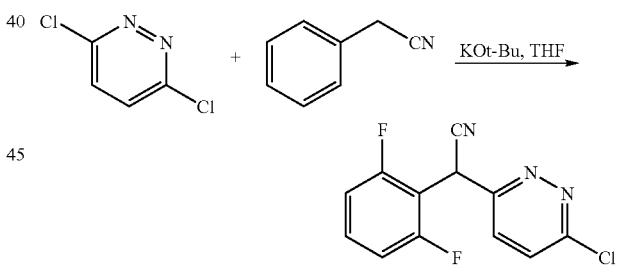

To a stirred solution of the appropriate phenylacetonitrile in rigorously degassed THF (approximately 10 mL/g) under N$_2$ at 0° C. was added dropwise a 1M solution of potassium t-butoxide in THF (1.1 eq.). After stirring at 0° C. for 30 minutes a solution of 3,6-dichloropyridazine (1 eq.) in rigorously degassed THF (approximately 10 mL/g) was added. The solution was stirred at room temperature for 17 hours and was then quenched with saturated aqueous ammonium chloride (approximately 20 mL/g). The mixture was filtered and the precipitate was washed with ethyl acetate (approximately 20 mL/g). Water (approximately 20 mL/g) was added to the filtrate and the organic layer was collected and the aqueous layer re-extracted with ethyl acetate (approximately 20 mL/g). The combined organic layer was washed with saturated aqueous brine solution (approximately 20 mL/g), dried over MgSO$_4$ and concentrated in vacuo to give the crude reaction product, which was purified by column chromatography using various ratios of ethyl acetate:hexane as eluant.

Part B: Synthesis of 2-(6-Chloropyridazin-3-yl)-2-(2,6-difluorophenyl)-acetamide

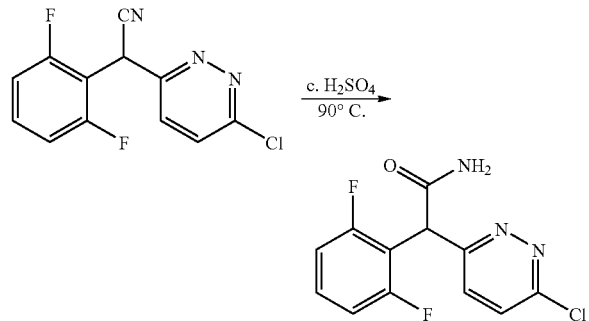

The 2-aryl-2-(6-chloro-pyridazin-2,3-yl) acetonitrile (1 eq.) was dissolved in concentrated sulfuric acid (approximately 10 mL/g) at room temperature, and the solution was heated to 90° C. and maintained at this temperature for 15 minutes. The reaction mixture was then poured slowly onto crushed ice (approximately 25 g/g of 2-aryl-2-(6-chloro-pyridazin-2,3-yl) acetonitrile used). Ethyl acetate (approximately 25 mL/g) was added, the organic layer was collected, and the aqueous layer re-extracted with ethyl acetate (approximately 25 mL/g). The combined organic layer was dried over MgSO₄ and concentrated in vacuo to give the reaction product, which typically did not require further purification.

EXAMPLE 7

Method A: Synthesis of 2-(2,6-Difluoro-phenyl)-2-(6-arylsulfanyl-pyridazin-3-yl)-acetamide Using Sodium Hydride as Base

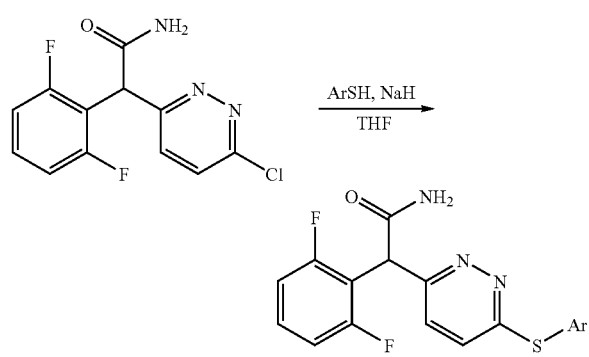

To a stirred suspension of sodium hydride (1.3 eq.) in anhydrous THF (approximately 200 mL/g) at room temperature under $N_2$ was added dropwise a solution of the appropriate thiophenol (1.3 eq.) in anhydrous THF approximately 50 mL/g). The solution was stirred at room temperature for 30 minutes, after which time a solution of 2-aryl-2-(6-chloro-pyridazin-2,3-yl) acetamide (1 eq.) in anhydrous THF (approximately 50 mL/g) was added. The solution was then heated to 65° C. for 17 hours. The reaction was cooled and saturated aqueous ammonium chloride solution and dichloromethane (DCM; equal volumes, approximately 100 mL/g of 2-aryl-2-(6-chloro-pyridazin-2,3-yl) acetamide used) were added. The organic layer was collected and the aqueous layer re-extracted with DCM (approximately 100 mL/g). The combined organic layer was washed with saturated aqueous brine solution (approximately 100 mL/g), dried over MgSO₄ and concentrated in vacuo to give the crude reaction product, which was typically purified by column chromatography using various ratios of ethyl acetate:hexane as eluant. One having ordinary skill in the art may synthesize analogous compounds, such as compounds comprising a heteroaryl group at $R^3$, following the teachings of the specification. In addition, one having ordinary skill in the art may synthesize analogous compounds comprising a substituted amide (a mono- or di-substituted amide) following the teachings of the specification.

Method B: Synthesis of 2-(2,6-Difluoro-phenyl)-2-(6-alkylsulfanyl-pyridazin-3-yl)-acetamide Using K-Selectride as Base (Fujimoto et al., Tet. Lett., 1999, 40, 5565)

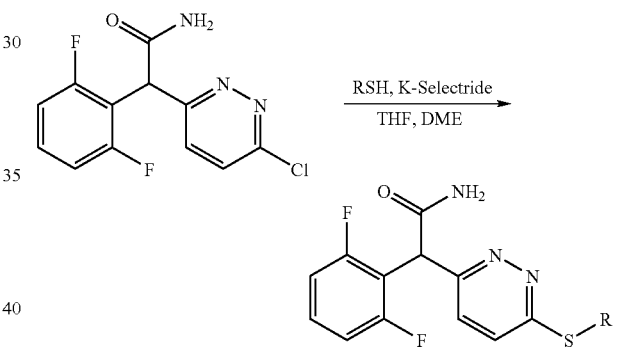

To a stirred solution of the appropriate thiol (1.1 eq.) in anhydrous DME (approximately 100 mL/g) at 0° C. under $N_2$ was added dropwise a 1M solution of K-Selectride in THF (1.1 eq.). The solution was stirred at 0° C. for 30 minutes, after which time a solution of 2-aryl-2-(6-chloro-pyridazin-2,3-yl) acetamide (1 eq.) in anhydrous DME (approximately 50 mL/g) was added. The solution was allowed to warm to room temperature and was stirred for 17 hours. A 1M aqueous solution of sodium hydroxide and ethyl acetate (equal volumes, approximately 100 mL/g of 2-aryl-2-(6-chloro-pyridazin-2,3-yl) acetamide used) was added. The organic layer was collected and the aqueous layer re-extracted with ethyl acetate (approximately 100 mL/g). The combined organic layer was washed with saturated aqueous brine solution (approximately 100 mL/g), dried over MgSO₄ and concentrated in vacuo to give the crude reaction product, which was typically purified by column chromatography using various ratios of ethyl acetate:hexane as eluant. One having ordinary skill in the art may synthesize analogous compounds, particularly alkane thiols, following the teachings of the specification. One having ordinary skill in the art may synthesize analogous compounds comprising a substituted amide (a mono- or di-substituted amide) following the teachings of the specification.

EXAMPLE 8

Oxidations of
2-Aryl-2-(6-Thioaryl/Thioalkyl-Pyridazin-2,3-yl)
Acetamides

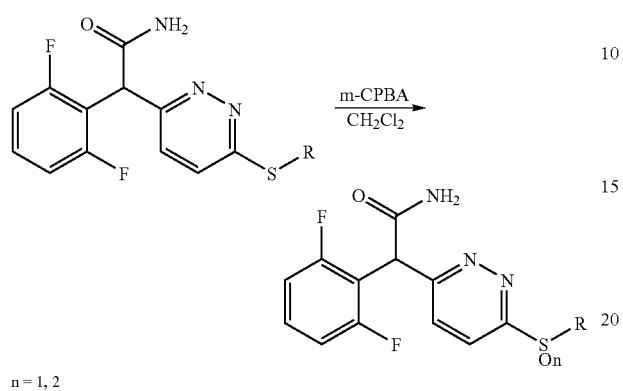

n = 1, 2

To a stirred solution of the 2-aryl-2-(6-thiophenyl-pyridazin-2,3-yl) acetamide (1 eq.) in anhydrous DCM (approximately 100 mL/g) at 0° C. under $N_2$ was added dropwise a solution of m-CPBA (1.1 eq. of approximately 50% w/w) in anhydrous DCM (approximately 50 mL/g). The solution was allowed to warm slowly to room temperature for 17 hours. Saturated aqueous sodium carbonate solution (approximately 100 mL/g of 2-aryl-2-(6-thioaryl/thioalkyl-pyridazin-2,3-yl) acetamide used) was added. The organic layer was removed and the aqueous layer re-extracted with DCM (approximately 100 mL/g). The combined organic layer was dried over $MgSO_4$ and concentrated in vacuo to give the reaction product, which was not further purified. One having ordinary skill in the art may synthesize analogous compounds following the teachings of the specification.

EXAMPLE 9

Synthesis of p38 Inhibitor Compound 101, (6-(2,6-Difluorophenylamino)-pyridin-3-yl]-phenylmethanone)

Compound 101 was synthesized according to Example 1 using methyl benzoate as the methoxy arylcarbonyl.

EXAMPLE 10

Cloning of p38 Kinase in Insect Cells

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET-15b vector (Novagen). The baculovirus transfer vector, pVL-(His)$_6$-p38 was constructed by subcloning a XbaI-BamHI fragment of pET15b-(His)6-p38 into the complementary sites in plasmid pVL1392 (Pharmingen).

The plasmid pVL-(His)6-p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of *Spodoptera frugiperda* (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of *Autographa califonica* nuclear polyhedrosis virus (Pharmingen) and transfer vector pVL(His)6-p38 using Lipofectin (Invitrogen). The individual recombinant baculovirus clones were purified by plaque assay using 1% low melting agarose.

EXAMPLE 11

Expression and Purification of Recombinant p38 Kinase

*Trichoplusia ni* (Tn-368) High-Five™ cells (Invitrogen) were grown in suspension in Excel-405 protein free medium (JRH Bioscience) in a shaker flask at 27° C. Cells at a density of 1.5×10$^6$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the (His)$_6$-tagged p38 was thawed in 5 volumes of Buffer A (50 mM $NaH_2PO_4$ pH 8.0, 200 mM NaCl, 2 mM β-Mercaptoethanol, 10% Glycerol and 0.2 mM PMSF). After mechanical disruption of the cells in a microfluidizer, the lysate was centrifuged at 30,000×g for 30 minutes. The supernatant was incubated batchwise for 3-5 hours at 4° C. with Talon™ (Clontech) metal affinity resin at a ratio of 1 ml of resin per 2-4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidazole.

The (His)$_6$-p38 was eluted with Buffer A+100 mM imidazole and subsequently dialyzed overnight at 4° C. against 2 liters of Buffer B, (50 mM HEPES, pH 7.5, 25 mM β-glycerophosphate, 5% glycerol, 2 mM DTT). The His$_6$ tag was removed by addition of at 1.5 units thrombin (Calbiochem) per mg of p38 and incubation at 20° C. for 2-3 hours. The thrombin was quenched by addition of 0.2 mM PMSF and then the entire sample was loaded onto a 2 ml benzamidine agarose (American International Chemical) column.

The flow through fraction was directly loaded onto a 2.6×5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3-4 ml and applied to a 2.6×100 cm Sephacryl S-100HR (Pharmacia) column. The protein was eluted at a flow rate of 35 ml/hr. The main peak was pooled, adjusted to 20 mM DTT, concentrated to 10-80 mgs/ml and frozen in aliquots at −70° C. or used immediately.

EXAMPLE 12

Activation of p38 p38 was activated by combining 0.5 mg/ml p38 with 0.005 mg/ml DD-double mutant MKK6 in Buffer B+10 mM $MgCl_2$, 2 mM ATP, 0.2 mM $Na_2VO_4$ for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM $Na_2VO_4$ to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+ 1.1M$K_2HPO_4$. The protein was eluted with a 20 column volume linear gradient to Buffer D+50 mM $K_2HPO_4$. The double phosphorylated p38 eluted as the main peak and was pooled for dialysis against Buffer B+0.2 mM $Na_2VO_4$. The activated p38 was stored at −70° C.

EXAMPLE 13 p38 Inhibition Assays

A. Inhibition of Phosphorylation of EGF Receptor Peptide

This assay was carried out in the presence of 10 mM $MgCl_2$, 25 mM β-glycerophosphate, 10% glycerol and 100 mM HEPES buffer at pH 7.6. For a typical $IC_{50}$ determination, a stock solution was prepared containing all of the above components and activated p38 (5 nM). The stock solution was aliquotted into vials. A fixed volume of DMSO or inhibitor in DMSO (final concentration of DMSO in reaction was 5%) was introduced to each vial, mixed and incubated for 15 minutes at room temperature. EGF receptor peptide, KRELVEPLTPSGEAPNQALLR, a phosphoryl acceptor in p38-catalyzed kinase reaction (1), was added to each vial to a final concentration of 200 μM. The kinase reaction was initiated with ATP (100 μM) and the vials were incubated at 30° C. After 30 minutes, the reactions were quenched with equal volume of 10% trifluoroacetic acid (TFA).

The phosphorylated peptide was quantified by HPLC analysis. Separation of phosphorylated peptide from the unphosphorylated peptide was achieved on a reverse phase column (Deltapak, 5 μm, C18 100D, Part no. 011795) with a binary gradient of water and acetonitrile, each containing 0.1% TFA. $IC_{50}$ (concentration of inhibitor yielding 50% inhibition) was determined by plotting the percent (%) activity remaining against inhibitor concentration.

B. Inhibition of ATPase Activity

This assay is carried out in the presence of 10 mM $MgCl_2$, 25 mM β-glycerophosphate, 10% glycerol and 100 mM HEPES buffer at pH 7.6. For a typical Ki determination, the Km for ATP in the ATPase activity of activated p38 reaction is determined in the absence of inhibitor and in the presence of two concentrations of inhibitor. A stock solution is prepared containing all of the above components and activated p38 (60 nM). The stock solution is aliquotted into vials. A fixed volume of DMSO or inhibitor in DMSO (final concentration of DMSO in reaction was 2.5%) is introduced to each vial, mixed and incubated for 15 minutes at room temperature. The reaction is initiated by adding various concentrations of ATP and then incubated at 30° C. After 30 minutes, the reactions are quenched with 50 μl of EDTA (0.1 M, final concentration), pH 8.0. The product of p38 ATPase activity, ADP, is quantified by HPLC analysis.

Separation of ADP from ATP is achieved on a reversed phase column (Supelcosil, LC-18, 3 μm, part no. 5-8985) using a binary solvent gradient of following composition: Solvent A—0.1 M phosphate buffer containing 8 mM tetrabutylammonium hydrogen sulfate (Sigma Chemical Co., catalogue no. T-7158), Solvent B—Solvent A with 30% methanol.

Ki is determined from the rate data as a function of inhibitor and ATP concentrations.

p38 inhibitors of this invention will inhibit the ATPase activity of p38.

The p38 inhibitory activity of certain compounds of this invention are shown in Table 7. For p38 kinase $IC_{50}$ values, "+++" represents $\leq 1$ μM, "++" represents between 1.0 and 10 μM, and "+" represents $\geq 10$ μM. For p38 kinase $K_i$ values, "+++" represents $\leq 1$ μM, "++" represents between 1.0 and 10 μM, and "+" represents $\geq 10$ μM.

TABLE 7

| Cpd. No. | p38 $IC_{50}$ (μM) | p38 $K_i$ (μM) |
| --- | --- | --- |
| 101 | +++ | ND |
| 102 | +++ | ND |
| 103 | ++ | ND |
| 104 | +++ | ND |
| 105 | +++ | ND |
| 106 | +++ | ND |
| 107 | +++ | ND |
| 108 | +++ | ND |
| 109 | + | ND |
| 110 | +++ | ND |
| 111 | ++ | ND |
| 112 | +++ | ND |
| 113 | +++ | ND |
| 114 | +++ | ND |
| 115 | +++ | ND |
| 116 | +++ | ND |
| 117 | +++ | ND |
| 118 | ++ | ND |
| 119 | +++ | ND |
| 120 | ++ | ND |
| 201 | +++ | ND |
| 301 | ++ | ND |
| 401 | + | ND |
| 402 | + | ND |
| 501 | + | ND |
| 502 | + | ND |
| 503 | +++ | ND |
| 601 | ++ | ND |
| 602 | ++ | ND |
| 603 | ++ | ND |
| 604 | +++ | ND |
| 605 | +++ | ND |
| 606 | + | ND |
| 607 | +++ | ND |
| 608 | ++ | ND |
| 609 | ++ | ND |
| 610 | +++ | ND |
| 611 | +++ | ND |
| 612 | + | ND |
| 613 | +++ | ND |
| 614 | +++ | ND |
| 615 | + | ND |
| 616 | + | ND |
| 617 | ++ | ND |
| 618 | ++ | ND |
| 619 | +++ | ND |
| 620 | +++ | ND |
| 621 | ++ | ND |
| 622 | +++ | ND |
| 623 | +++ | ND |
| 624 | +++ | ND |

TABLE 7-continued

| Cpd. No. | p38 IC$_{50}$ (μM) | p38 K$_i$ (μM) |
|---|---|---|
| 625 | ND | ++ |
| 626 | ND | ++ |
| 627 | ND | ++ |
| 628 | ND | ++ |
| 629 | ND | ++ |
| 630 | ND | ++ |
| 631 | ND | ++ |
| 632 | ND | ++ |
| 633 | ND | ++ |
| 634 | ND | ++ |
| 635 | ND | ++ |

C. Inhibition of IL-1, TNF, IL-6 and IL-8 Production in LPS-Stimulated PBMCs

Inhibitors were serially diluted in DMSO from a 20 mM stock. At least 6 serial dilutions were prepared. Then 4× inhibitor stocks were prepared by adding 4 μl of an inhibitor dilution to 1 ml of RPMI1640 medium/10% fetal bovine serum. The 4× inhibitor stocks contained inhibitor at concentrations of 80 μM, 32 μM, 12.8 μM, 5.12 μM, 2.048 μM, 0.819 μM, 0.328 μM, 0.131 μM, 0.052 μM, 0.021 μM etc. The 4× inhibitor stocks were pre-warmed at 37° C. until use.

Fresh human blood buffy cells were separated from other cells in a Vacutainer CPT from Becton & Dickinson (containing 4 ml blood and enough DPBS without Mg$^{2+}$/Ca$^{2+}$ to fill the tube) by centrifugation at 1500×g for 15 min. Peripheral blood mononuclear cells (PBMCs), located on top of the gradient in the Vacutainer, were removed and washed twice with RPMI1640 medium/10% fetal bovine serum. PBMCs were collected by centrifugation at 500×g for 10 min. The total cell number was determined using a Neubauer Cell Chamber and the cells were adjusted to a concentration of 4.8×10$^6$ cells/ml in cell culture medium (RPMI1640 supplemented with 10% fetal bovine serum).

Alternatively, whole blood containing an anti-coagulant was used directly in the assay.

100 μl of cell suspension or whole blood were placed in each well of a 96-well cell culture plate. Then 50 μl of the 4× inhibitor stock was added to the cells. Finally, 50 μl of a lipopolysaccharide (LPS) working stock solution (16 ng/ml in cell culture medium) was added to give a final concentration of 4 ng/ml LPS in the assay. The total assay volume of the vehicle control was also adjusted to 200 μl by adding 50 μl cell culture medium. The PBMC cells or whole blood were then incubated overnight (for 12-15 hours) at 37° C./5% CO$_2$ in a humidified atmosphere.

The next day the cells were mixed on a shaker for 3-5 minutes before centrifugation at 500×g for 5 minutes. Cell culture supernatants were harvested and analyzed by ELISA for levels of IL-1□ (R & D Systems, Quantikine kits, #DBL50), TNF-□ (BioSource, #KHC3012), IL-6 (Endogen, #EH2-IL6) and IL-8 (Endogen, #EH2-IL8) according to the instructions of the manufacturer. The ELISA data were used to generate dose-response curves from which IC50 values were derived.

The p38 inhibitors of this invention will also inhibit phosphorylation of EGF receptor peptide, and will inhibit the production of IL-1, TNF and IL-6, as well as IL-8, in LPS-stimulated PBMCs or in whole blood.

D. Inhibition of IL-6 and IL-8 Production in IL-1-Stimulated PBMCs

This assay is carried out on PBMCs exactly the same as above except that 50 μl of an IL-1b working stock solution (2 ng/ml in cell culture medium) is added to the assay instead of the (LPS) working stock solution.

Cell culture supernatants are harvested as described above and analyzed by ELISA for levels of IL-6 (Endogen, #EH2-IL6) and IL-8 (Endogen, #EH2-IL8) according to the instructions of the manufacturer. The ELISA data are used to generate dose-response curves from which IC50 values were derived.

E. Inhibition of LPS-Induced Prostaglandin Endoperoxide Synthase-2 (PGHS-2, or COX-2) Induction in PBMCs Human peripheral mononuclear cells (PBMCs) are isolated from fresh human blood buffy coats by centrifugation in a Vacutainer CPT (Becton & Dickinson). 15×10$^6$ cells are seeded in a 6-well tissue culture dish containing RPMI 1640 supplemented with 10% fetal bovine serum, 50 U/ml penicillin, 50 μg/ml streptomycin, and 2 mM L-glutamine. Compounds are added at 0.2, 2.0 and 20 μM final concentrations in DMSO. LPS is then added at a final concentration of 4 ng/ml to induce enzyme expression. The final culture volume is 10 ml/well.

After overnight incubation at 37° C., 5% CO$_2$, the cells are harvested by scraping and subsequent centrifugation, the supernatant is removed, and the cells are washed twice in ice-cold DPBS (Dulbecco's phosphate buffered saline, BioWhittaker). The cells are lysed on ice for 10 min in 50 μl cold lysis buffer (20 mM Tris-HCl, pH 7.2, 150 mM NaCl, 1% Triton-X-100, 1% deoxycholic acid, 0.1% SDS, 1 mM EDTA, 2% aprotinin (Sigma), 10 μg/ml pepstatin, 10 μg/ml leupeptin, 2 mM PMSF, 1 mM benzamidine, 1 mM DTT) containing 1 μl Benzonase (DNAse from Merck). The protein concentration of each sample is determined using the BCA assay (Pierce) and bovine serum albumin as a standard. Then the protein concentration of each sample is adjusted to 1 mg/ml with cold lysis buffer. To 100 μl lysate an equal volume of 2×SDS PAGE loading buffer is added and the sample is boiled for 5 min. Proteins (30 μg/lane) are size-fractionated on 4-20% SDS PAGE gradient gels (Novex) and subsequently transferred onto nitrocellulose membrane by electrophoretic means for 2 hours at 100 mA in Towbin transfer buffer (25 mM Tris, 192 mM glycine) containing 20% methanol. After transfer, the membrane is pretreated for 1 hour at room temperature with blocking buffer (5% non-fat dry milk in DPBS supplemented with 0.1% Tween-20) and washed 3 times in DPBS/0.1% Tween-20. The membrane is incubated overnight at 4° C. with a 1:250 dilution of monoclonal anti-COX-2 antibody (Transduction Laboratories) in blocking buffer. After 3 washes in DPBS/0.1% Tween-20, the membrane is incubated with a 1:1000 dilution of horseradish peroxidase-conjugated sheep antiserum to mouse Ig (Amersham) in blocking buffer for 1 h at room temperature. Then the membrane is washed again 3 times in DPBS/0.1% Tween-20. An ECL detection system (SuperSignal™ CL-HRP Substrate System, Pierce) is used to determine the levels of expression of COX-2.

While we have hereinbefore presented a number of embodiments of this invention, it is apparent that our basic construction can be altered to provide other embodiments which utilize the methods of this invention

We claim:

1. A compound of the formula:

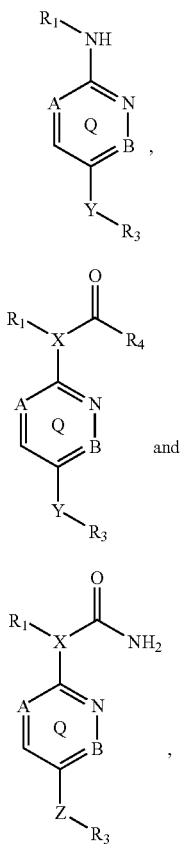

or a pharmaceutically acceptable salt thereof, wherein:
A is CR;
B is CR;
X is N or CH;
Y is C(O), CHOH, S, S(O), S(O)$_2$, or Z;
Z is —S—[(C$_1$-C$_3$)-alkyl]-, —O—[(C$_1$-C$_3$)-alkyl]-, —NH—[(C$_1$-C$_3$)-alkyl]-, —[(C$_2$-C$_3$)-alkenyl]-, —[(C$_2$-C$_3$)-alkynyl]-, —O—[(C$_2$-C$_3$)-alkenyl]-, —O—[(C$_2$-C$_3$)-alkynyl]-, —S—[(C$_2$-C$_3$)-alkenyl]-, —S—[(C$_2$-C$_3$)-alkynyl]-, —NH—[(C$_2$-C$_3$)-alkenyl]-, —NH—[(C$_2$-C$_3$)-alkynyl]-, —[(C$_1$-C$_3$)-alkyl]-S—, —[(C$_1$-C$_3$)-alkyl]-O—, —[(C$_1$-C$_3$)-alkyl]-NH—, —[(C$_2$-C$_3$)-alkenyl]-O—, —[(C$_2$-C$_3$)-alkynyl]-O—, —[(C$_2$-C$_3$)-alkenyl]-S—, —[(C$_2$-C$_3$)-alkynyl]-S—, —[(C$_2$-C$_3$)-alkenyl]-NH— or —[(C$_2$-C$_3$)-alkynyl]-NH—;

the carbon atoms of Q may be optionally substituted with R;

R$_1$ is selected from aryl, heteroaryl, carbocyclyl, heterocyclyl or C$_{1-10}$ aliphatic, any of which may be optionally substituted;

R$_3$ is selected from C$_{2-10}$ aliphatic, phenyl, pyridyl, thienyl, furanyl, benzothienyl, or naphthyl and optionally contains up to 3 substituents, each of which is independently selected from chloro, fluoro, bromo, methyl, ethyl, isopropyl, —OCH$_3$, —OH, —NH$_2$, —CF$_3$, —OCF$_3$, —SCH$_3$, —C(O)OH, —C(O)OCH$_3$, —CH$_2$NH$_2$, —N(CH$_3$)$_2$, pyrrolyl, —CH$_2$-pyrrolidine, —CH$_2$OH, and phenyl;

R$_4$ is selected from NHR$_5$, N(R$_5$)$_2$, OR$_5$, C(O)OR$_5$, —C(O)R$_5$ or R$_6$;

each R$_5$ is independently selected from aryl, heteroaryl, carbocyclyl, heterocyclyl or C$_{1-5}$ aliphatic;

R$_6$ is selected from aryl, heteroaryl, carbocyclyl, heterocyclyl or C$_{1-5}$ aliphatic, any of which may be optionally substituted;

each R is independently selected from H, halo or a straight or branched chain C$_1$-C$_4$ alkyl;

each of R$_1$, R$_5$ and R$_6$ are independently and optionally substituted with up to 4 substituents, each of which is independently selected from halo; C$_1$-C$_3$ alkyl optionally substituted with NR'$_2$, OR', CO$_2$R' or CONR'$_2$; O—(C$_1$-C$_3$)-alkyl optionally substituted with NR'$_2$, OR', CO$_2$R' or CONR'$_2$; R'; NR'$_2$; OCF$_3$; CF$_3$; NO$_2$; CO$_2$R'; CONHR'; SR'; COR'; S(O$_2$)N(R')$_2$; SCF$_3$; CN; N(R')C(O)R'; N(R')C(O)OR'; N(R')C(O)C(O)R'; N(R')S(O$_2$)R'; OR'; OC(O)R'; OP(O)$_3$H$_2$; N=CH—N(R')$_2$; 3,4-methylenedioxy; —NH—C(O)O—CH$_2$-4-pyridine, —NH—C(O)CH$_2$-morpholine; —NH—C(O)CH$_2$-piperazine; or —NH—C(O)CH$_2$-pyrrolidine;

R$_3$ is optionally substituted with up to 4 substituents, each of which is independently selected from halo; C$_1$-C$_3$ straight or branched alkyl optionally substituted with N(R')$_2$, OR', CO$_2$R', S(O$_2$)N(R')$_2$, N=CH—N(R')$_2$, R', or CON(R')$_2$; O—(C$_1$-C$_3$)-alkyl optionally substituted with N(R')$_2$, OR', CO$_2$R', S(O$_2$)N(R')$_2$, N=CH—N(R')$_2$, R', or CON(R')$_2$; N(R')$_2$; OCF$_3$; CF$_3$; NO$_2$; CON(R')$_2$; R'; OR'; SR'; COR'; C(O)OR'; S(O$_2$)N(R')$_2$; SCF$_3$; N=CH—N(R')$_2$; or CN;

R' is selected from hydrogen; (C$_1$-C$_3$)-alkyl; (C$_2$-C$_3$)-alkenyl or alkynyl; a 5-8 membered aryl ring system, a 5-8 membered heteroaryl ring system or a 5-6 membered heterocyclic ring system, any of which may be independently and optionally substituted with 1 to 3 substituents independently selected from halo, methoxy, cyano, nitro, amino, hydroxy, methyl or ethyl;

provided that in compounds of Formula I, when Y is CHOH and R$_3$ is a substituted phenyl, then R$_1$ is not cyclopropyl or benzyl;

when Y is SO$_2$, and R$_3$ is morpholino or is N-methylpiperazino, then R$_1$ is not meta-trifluoromethyiphenyl;

when Y is C=O, and R$_3$ is 4H, 10H-3,3a,9-triaza-benzo[f]azulen-9-yl or is 5H,11H-Benzo[e]pyrrolo[1,2-a][1,4]diazepin-10-yl, then R$_1$ is not C$_4$-C$_7$ alkyl, cyclohexyl, cyclohexyl-CH$_2$—, 2-tolyl-CH$_2$—, phenyl-(CH$_2$)$_2$—, phenyl-(CH$_2$)$_3$—, 2-tolyl-Cl—, 2-thipheneyl-CH$_2$—, 2-thipheneyl-(CH$_2$)$_2$—, 2-pyridinyl-(CH$_2$)$_2$—, or substituted phenyl, benzoyl, furanoyl, or 3-pyridinyl-C(O)—; and further provided that in compounds of Formulae I and II, when X, if present, is N, Y is C$_2$-C$_3$ alkynyl, R$_4$, if present, is CH$_3$, and R$_3$ is (CH$_2$)$_4$OH or is (CH$_2$)$_4$-pyridine or is (CH$_2$)$_4$-imidazole, then R$_1$ is not 4-isopropylphenyl.

2. The compound according to claim 1, wherein R$_1$ is aryl or heteroaryl.

3. The compound according to claim 2, wherein R$_1$ is a substituted aryl.

4. The compound according to claim 1, wherein Y is C(O).

5. The compound according to claim 1, wherein X, if present, is N.

6. The compound according to claim 1, having the formula

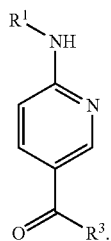
(Ia)

7. The compound according to claim 1, having the formula

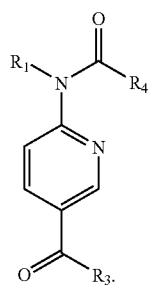
(IIa)

8. The compound according to claim 1, wherein $R_1$ is selected from phenyl or pyridyl containing 1 to 3 substituents independently selected from chloro, fluoro, bromo, —$CH_3$, —$OCH_3$, —OH, —$CF_3$, —$OCF_3$, —$O(CH_2)_2CH_3$, $NH_2$, 3,4-methylenedioxy, —$N(CH_3)_2$, —NH—$S(O)_2$-phenyl, —NH—C(O)O—$CH_2$-4-pyridine, —NH—C(O)$CH_2$-morpholine,
- —NH—C(O)$CH_2$—$N(CH_3)_2$, —NH—C(O)$CH_2$-piperazine,
- —NH—C(O)$CH_2$-pyrrolidine, —NH—C(O)C(O)-morpholine,
- —NH—C(O)C(O)-piperazine, —NH—C(O)C(O)-pyrrolidine,
- —O—C(O)$CH_2$—$N(CH_3)_2$, or —O—$(CH_2)_2$—$N(CH_3)_2$.

9. The compound according to claim 1, wherein $R_3$ is selected from:

n-butyl, isobutyl, unsubstituted phenyl,

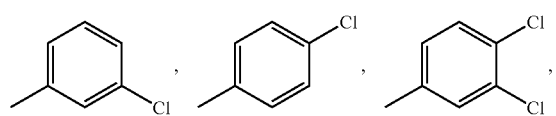

-continued

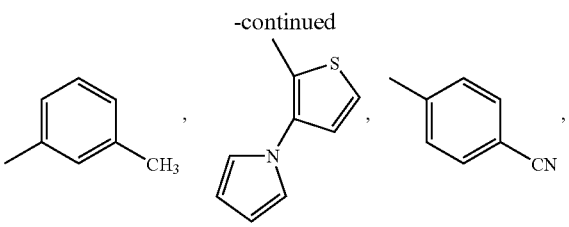

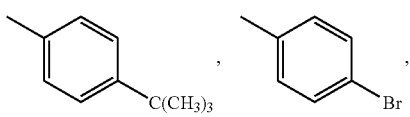

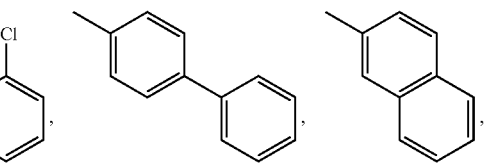

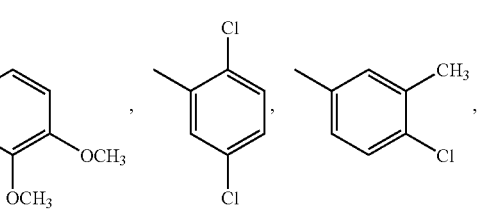

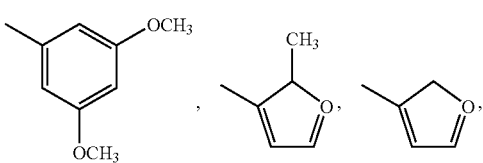

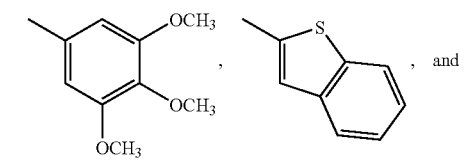

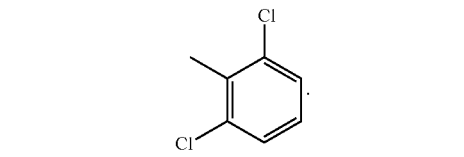, and

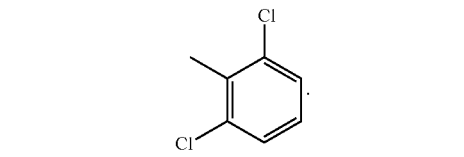

10. The compound according to claim 1, wherein $R_4$ is selected from phenyl, —$C(CH_3)_3$, —$CH_2OCH_3$, —$CH_3$, 4-bromophenyl, cyclohexane, —$CH_2CH_2C(O)OCH_3$, 3-trifluoromethylphenyl, 3-trifluoromethyl-4-fluorophenyl, —C(O)$OCH_2CH_3$, —$CH_2CH(CH_3)_2$, —$CH_2CH_2$-phenyl, —$CH_2$-4-fluorophenyl, —$OCH_2$-phenyl, —O-4-fluorophenyl,

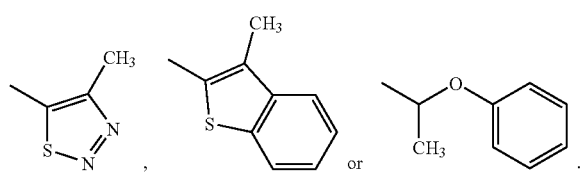
11. The compound according to claim 1, wherein the compound is selected from any one of the following compounds:
| Cpd. No. | Structure |
|---|---|
| 101 | 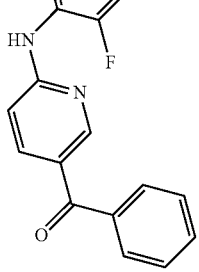 |
| 102 |  |
| 103 | 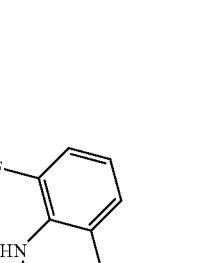 |
| 104 | 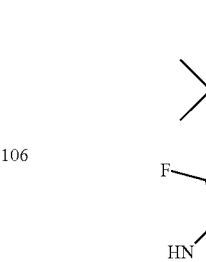 |
| 105 | 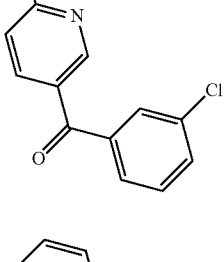 |
| 106 | 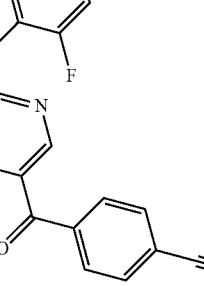 |
| 107 | 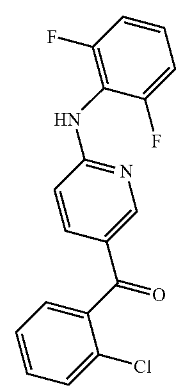 |

-continued
| Cpd. No. | Structure |
|---|---|
| 108 | 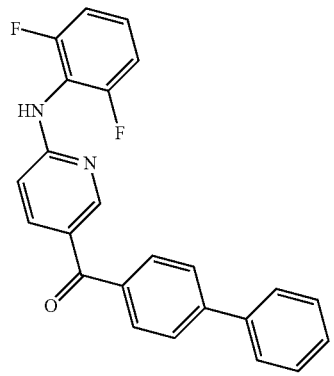 |
| 109 | 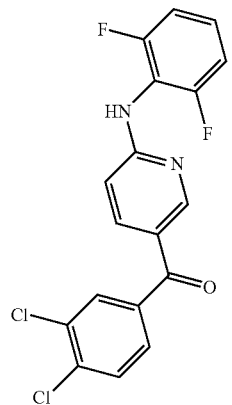 |
| 110 | 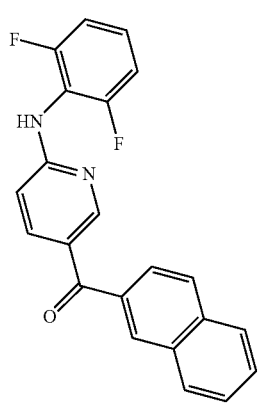 |
-continued
| Cpd. No. | Structure |
|---|---|
| 111 | 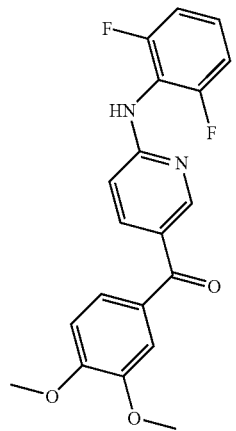 |
| 112 | 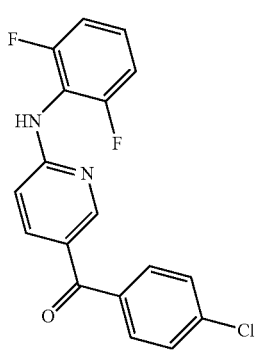 |
| 113 | 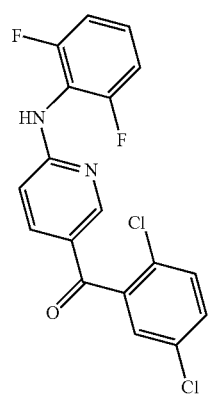 |
| 114 | 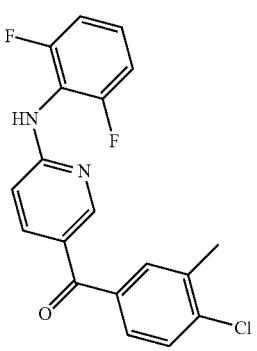 |

-continued
| Cpd. No. | Structure |
|---|---|
| 115 | 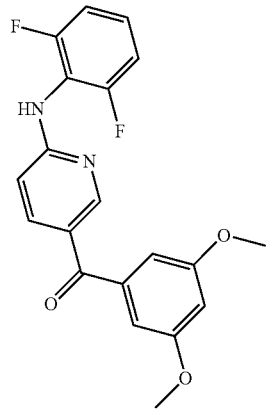 |
| 116 | 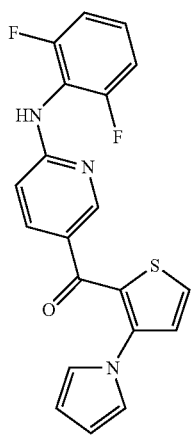 |
| 117 | 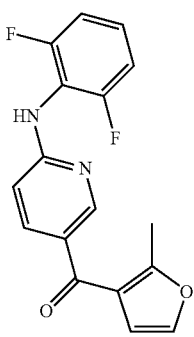 |
-continued
| Cpd. No. | Structure |
|---|---|
| 118 | 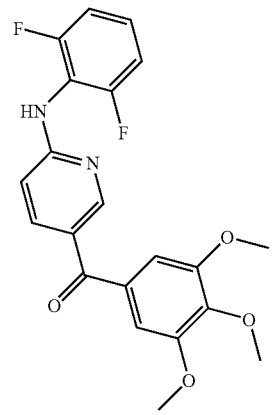 |
| 119 | 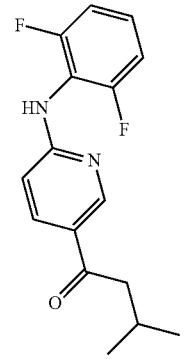 |
| 120 | 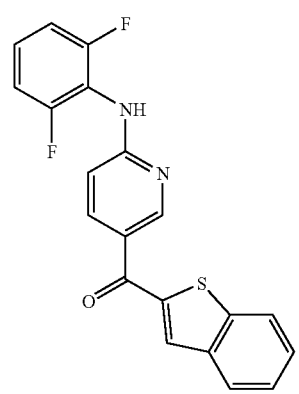 |
| 201 | 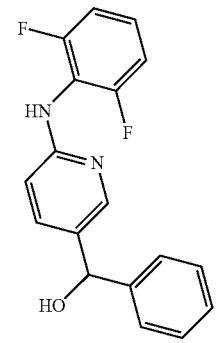 |

-continued
| Cpd. No. | Structure |
|---|---|
| 402 | 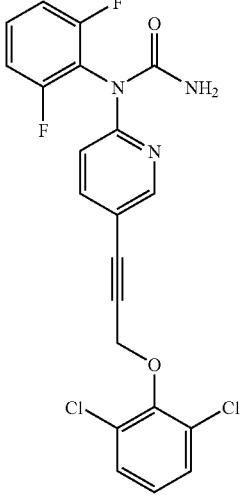 |
| 501 | 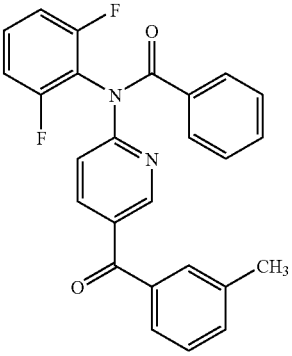 |
| 502 | 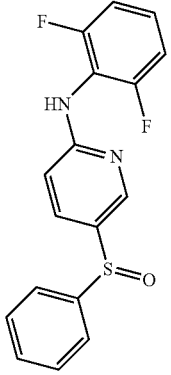 |
| 503 | 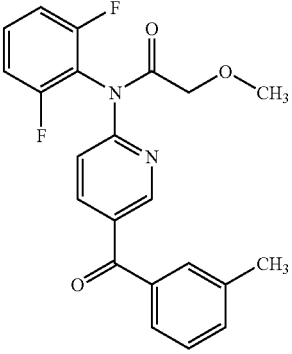 |
-continued
| Cpd. No. | Structure |
|---|---|
| 601 | 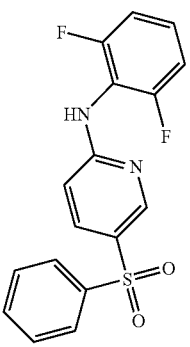 |
| 602 | 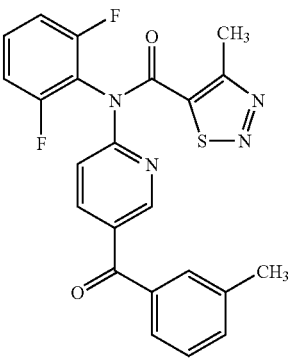 |
| 603 | 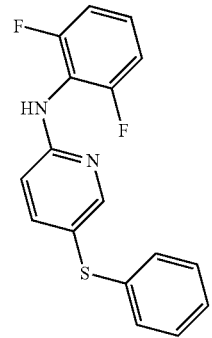 |
| 604 | 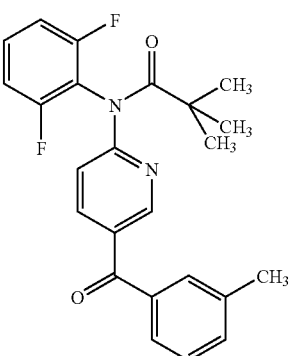 |

-continued
| Cpd. No. | Structure |
|---|---|
| 605 | 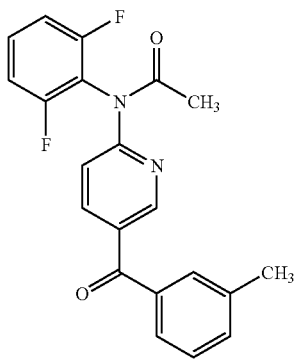 |
| 606 | 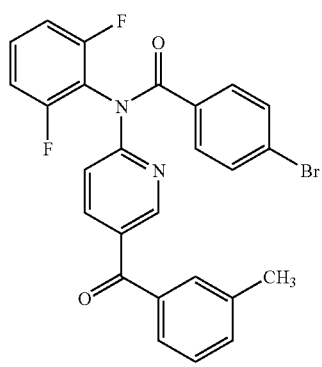 |
| 607 | 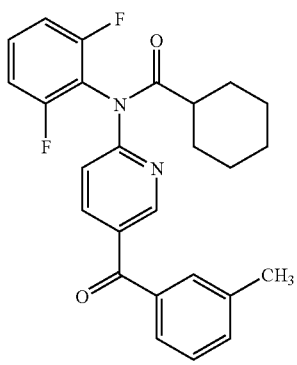 |
| 608 | 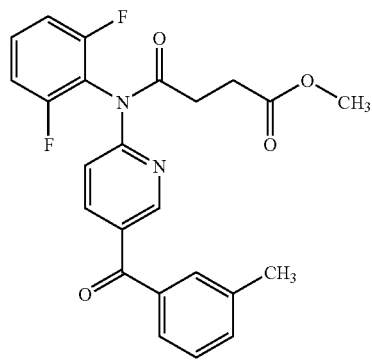 |
-continued
| Cpd. No. | Structure |
|---|---|
| 609 | 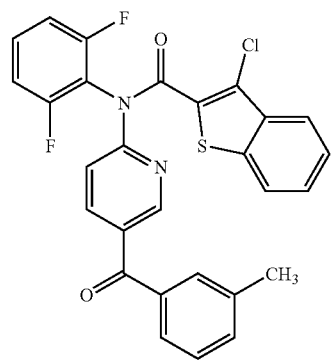 |
| 610 | 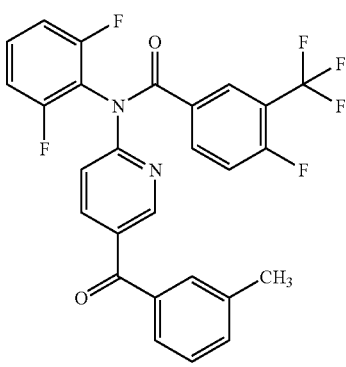 |
| 611 | 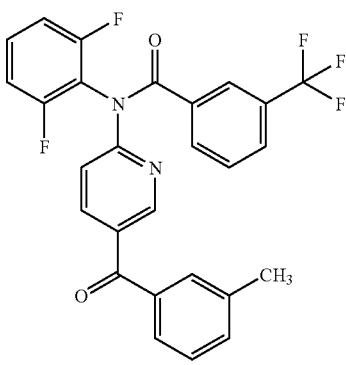 |
| 612 | 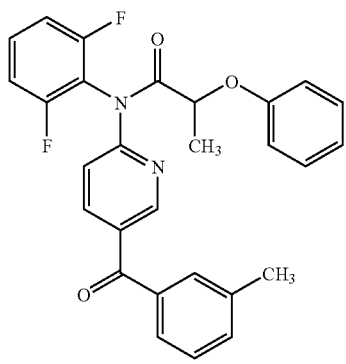 |

-continued

| Cpd. No. | Structure |
|---|---|
| 613 | (structure) |
| 614 | (structure) |
| 615 | (structure) |
| 616 | (structure) |

-continued

| Cpd. No. | Structure |
|---|---|
| 617 | (structure) |
| 618 | (structure) |
| 619 | (structure) |

-continued
| Cpd. No. | Structure |
|---|---|
| 620 | 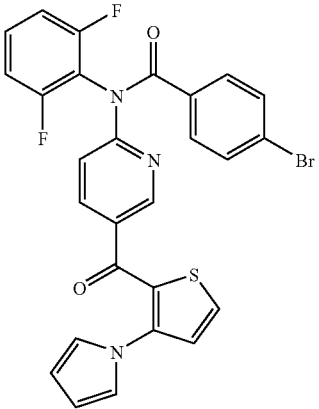 |
| 621 | 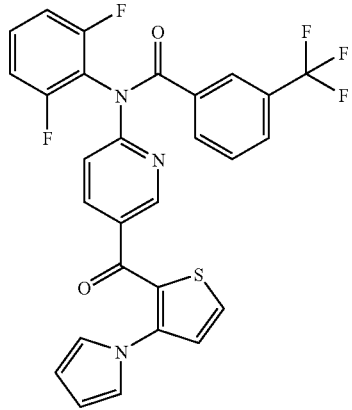 |
| 622 | 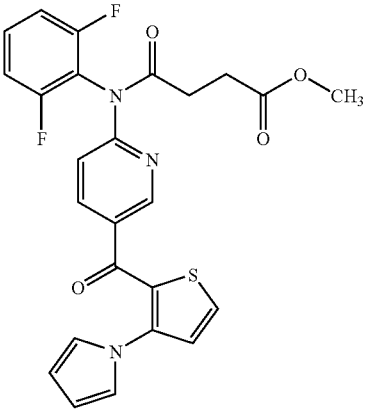 |
-continued
| Cpd. No. | Structure |
|---|---|
| 623 | 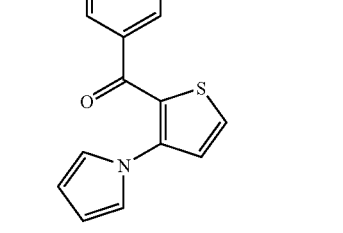 |
| 624 | 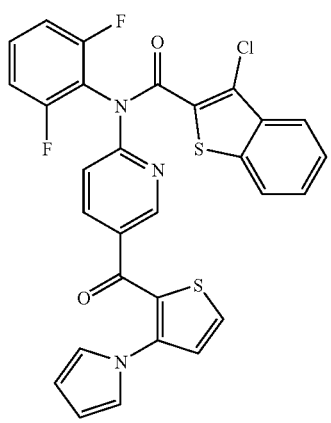 |
| 625 | 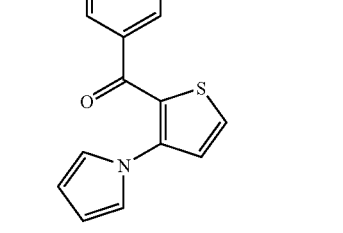 |
| 626 | 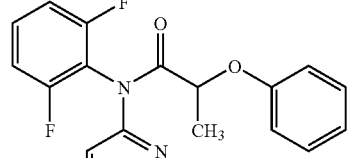 |

-continued
| Cpd. No. | Structure |
|---|---|
| 627 | 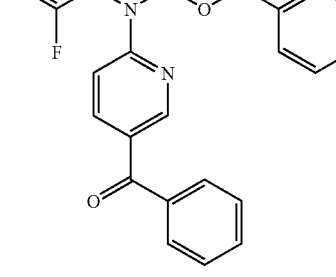 |
| 628 | 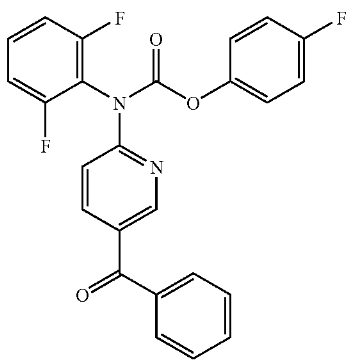 |
| 629 | 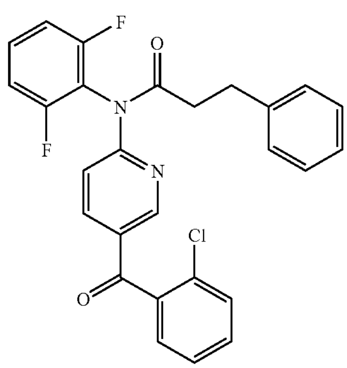 |
| 630 | 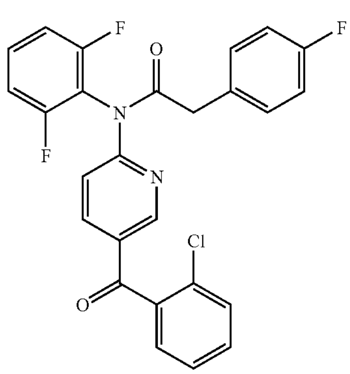 |
-continued
| Cpd. No. | Structure |
|---|---|
| 631 | 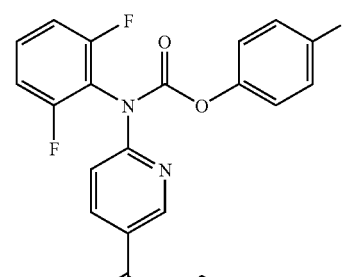 |
| 632 | 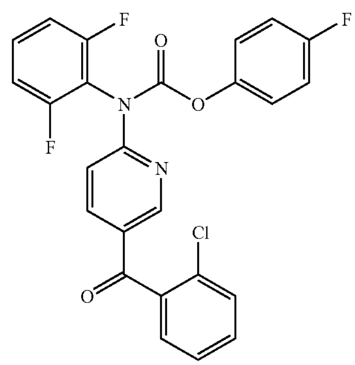 |
| 633 | 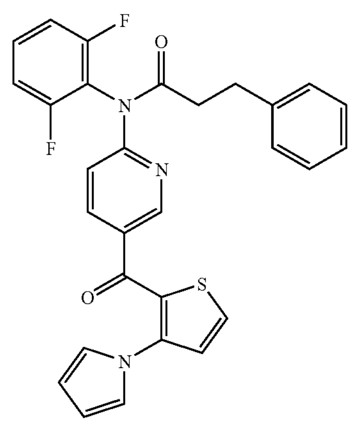 |
| 634 | 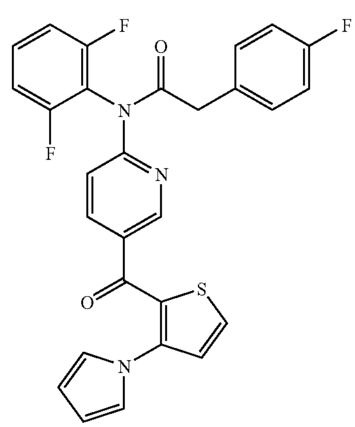 |

| Cpd. No. | Structure |
|---|---|
| 635 | 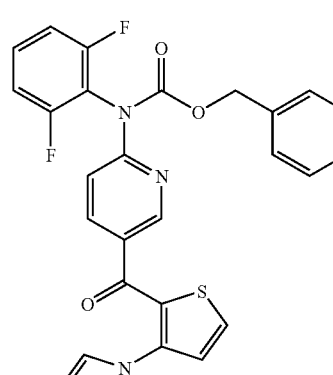 |

12. A pharmaceutical composition comprising an amount of a compound according to claim 1 effective to inhibit p38, and a pharmaceutically acceptable carrier.

13. A method of treating cerebral ischemia, reperfusion/ischemia in stroke, myocardial ischemia, renal ischemia, rheumatoid arthritis, or Crohn's disease in a patient, said method comprising administering to said patient a composition according to claim 12.

14. The method according to claim 13, wherein said method is used to treat rheumatoid arthritis or Crohn's disease.

15. The method according to claim 13, wherein said method is used to treat ischemia/reperfusion in stroke, myocardial ischemia, or renal ischemia.

* * * * *

UNITED STATES PATENT AND TRADEMARK OFFICE
CERTIFICATE OF CORRECTION

PATENT NO. : 7,271,181 B2
APPLICATION NO. : 10/144153
DATED : September 18, 2007
INVENTOR(S) : Jeremy Green et al.

It is certified that error appears in the above-identified patent and that said Letters Patent is hereby corrected as shown below:

Title page, item [57], line 2: insert --in-- after "involved".

Column 48, line 47: change "meta-trifluoromethyiphenyl" to --meta-trifluoromethylphenyl--.

Signed and Sealed this

First Day of July, 2008

JON W. DUDAS
*Director of the United States Patent and Trademark Office*